(12) United States Patent
Motzer et al.

(10) Patent No.: US 10,571,390 B2
(45) Date of Patent: Feb. 25, 2020

(54) COMPOSITE INSPECTION

(71) Applicants: The Boeing Company, Chicago, IL (US); University of Washington, Seattle, WA (US)

(72) Inventors: William P. Motzer, Charleston, SC (US); Gary Ernest Georgeson, Tacoma, WA (US); Jill Paisley Bingham, Seattle, WA (US); Steven Kenneth Brady, Renton, WA (US); Alan F. Stewart, Seattle, WA (US); James C. Kennedy, Summerville, SC (US); Ivan Pelivanov, Seattle, WA (US); Matthew O'Donnell, Seattle, WA (US); Jeffrey Reyner Kollgaard, Seattle, WA (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 15/070,583

(22) Filed: Mar. 15, 2016

(65) Prior Publication Data
US 2017/0176322 A1 Jun. 22, 2017

Related U.S. Application Data

(60) Provisional application No. 62/270,554, filed on Dec. 21, 2015.

(51) Int. Cl.
*G01N 21/17* (2006.01)

(52) U.S. Cl.
CPC . *G01N 21/1702* (2013.01); *G01N 2021/1706* (2013.01)

(58) Field of Classification Search
CPC .......... G01N 21/1702; G01N 29/2418; G01N 2021/1706; G01N 29/0672; G01N 29/04; G01N 29/24; G01N 29/44; G01N 29/46
See application file for complete search history.

(56) References Cited

U.S. PATENT DOCUMENTS

| 4,665,228 A | 4/1987 | Shimura et al. |
| 5,010,885 A | 4/1991 | Fink et al. |
| 5,373,460 A * | 12/1994 | Marks, II ............. G06F 17/141 |
| | | 704/E11.002 |

(Continued)

FOREIGN PATENT DOCUMENTS

JP 2011058937 A 3/2011

OTHER PUBLICATIONS https://en.wikipedia.org/wiki/Discrete_Fourier_transform.*
(Continued)

*Primary Examiner* — Mohamed K Amara
(74) *Attorney, Agent, or Firm* — Yee & Associates, P.C.

(57) ABSTRACT

A method of detecting local material changes in a composite structure is presented. A pulsed laser beam is directed towards the composite structure comprised of a number of composite materials. Wide-band ultrasonic signals are formed in the composite structure when radiation of the pulsed laser beam is absorbed by the composite structure. The wide-band ultrasonic signals are detected to form data. The data is processed to identify a local frequency value for the composite structure. The local frequency value is used to determine if local material changes are present in the number of composite materials.

21 Claims, 12 Drawing Sheets

(56) References Cited

U.S. PATENT DOCUMENTS

| | | | |
|---|---|---|---|
| 5,679,899 A | 10/1997 | Webster et al. | |
| 6,014,621 A * | 1/2000 | Chen | G10L 19/0212 |
| | | | 704/219 |
| 6,405,069 B1 * | 6/2002 | Oraevsky | A61B 5/0095 |
| | | | 367/7 |
| 6,954,662 B2 * | 10/2005 | Freger | A61B 5/14532 |
| | | | 600/316 |
| 6,981,417 B1 * | 1/2006 | Oravecz | G01N 29/0609 |
| | | | 73/612 |
| 7,000,475 B2 * | 2/2006 | Oravecz | G01N 29/0609 |
| | | | 73/602 |
| 7,142,904 B1 * | 11/2006 | Tucker | A61B 5/053 |
| | | | 600/407 |
| 7,345,279 B2 * | 3/2008 | Mueller | G01J 9/04 |
| | | | 250/341.1 |
| 7,378,658 B2 * | 5/2008 | Mueller | G01J 3/42 |
| | | | 250/330 |
| 7,586,618 B2 * | 9/2009 | Marks | G01J 3/4412 |
| | | | 356/451 |
| 7,610,074 B2 * | 10/2009 | Boppart | A61B 5/416 |
| | | | 424/9.1 |
| 7,623,908 B2 * | 11/2009 | Boppart | G01J 3/44 |
| | | | 600/477 |
| 7,751,057 B2 * | 7/2010 | Oldenburg | A61B 5/0066 |
| | | | 356/497 |
| 7,787,129 B2 * | 8/2010 | Zysk | A61B 5/0084 |
| | | | 356/481 |
| 7,858,940 B2 * | 12/2010 | Ouchi | G01N 21/4795 |
| | | | 250/341.1 |
| RE42,497 E * | 6/2011 | Wax | G01N 15/0211 |
| | | | 356/497 |
| 8,115,934 B2 * | 2/2012 | Boppart | A61B 5/0066 |
| | | | 356/479 |
| 8,129,684 B2 * | 3/2012 | Mueller | G01N 21/3581 |
| | | | 250/330 |
| 8,235,897 B2 * | 8/2012 | Gal | A61B 5/6816 |
| | | | 600/365 |
| 8,392,176 B2 * | 3/2013 | Garudadri | G10L 19/08 |
| | | | 329/315 |
| 8,402,399 B2 * | 3/2013 | Hurley | G03F 1/70 |
| | | | 716/50 |
| 8,494,622 B2 * | 7/2013 | Gu | A61B 5/0472 |
| | | | 600/509 |
| 8,537,366 B2 * | 9/2013 | Wax | G01B 9/02091 |
| | | | 356/456 |
| 8,708,496 B2 * | 4/2014 | Gu | G01M 11/025 |
| | | | 351/246 |
| 8,969,806 B2 * | 3/2015 | Fukuma | G01J 3/06 |
| | | | 250/339.07 |
| 8,983,580 B2 * | 3/2015 | Boppart | A61B 5/0066 |
| | | | 600/473 |
| 9,057,595 B2 * | 6/2015 | Hall | G01B 9/02091 |
| 9,097,684 B2 * | 8/2015 | Tomioka | G01N 21/3581 |
| 9,164,066 B1 | 10/2015 | Bossi et al. | |
| 9,179,843 B2 * | 11/2015 | Moghaddam | A61B 5/0075 |
| 9,188,566 B2 | 11/2015 | Georgeson et al. | |
| 9,201,052 B2 * | 12/2015 | Ho | G01N 21/3581 |
| 9,220,411 B2 * | 12/2015 | Hillman | A61B 5/0059 |
| 9,250,213 B1 | 2/2016 | Bossi et al. | |
| 9,506,740 B2 * | 11/2016 | Brezinski | A61B 5/0066 |
| 9,823,127 B2 * | 11/2017 | Wax | G01J 3/2823 |
| 9,905,044 B1 * | 2/2018 | Carmi | G06T 15/08 |
| 10,175,178 B2 * | 1/2019 | Tonn | G01B 9/02091 |
| 10,292,595 B2 * | 5/2019 | Wax | A61B 5/0084 |
| 10,309,893 B2 * | 6/2019 | Georgeson | G01N 21/1702 |
| 10,345,267 B2 * | 7/2019 | O'Donnell | G01N 29/0645 |
| 2002/0016335 A1 * | 2/2002 | Youle | A61K 31/00 |
| | | | 514/313 |
| 2006/0235621 A1 * | 10/2006 | Cole | G01N 21/4795 |
| | | | 702/19 |
| 2006/0285635 A1 * | 12/2006 | Boppart | A61B 5/0066 |
| | | | 378/22 |
| 2007/0157730 A1 * | 7/2007 | Ochiai | F22B 37/003 |
| | | | 73/627 |
| 2009/0301202 A1 * | 12/2009 | Bisiaux | G01N 29/041 |
| | | | 73/622 |
| 2010/0191792 A1 * | 7/2010 | Brown | G06F 17/148 |
| | | | 708/404 |
| 2012/0050224 A1 * | 3/2012 | Chung | G06F 3/0418 |
| | | | 345/175 |
| 2013/0088724 A1 | 4/2013 | Dubois et al. | |
| 2014/0116146 A1 | 5/2014 | Bossi et al. | |
| 2014/0257079 A1 * | 9/2014 | Irisawa | A61B 5/0095 |
| | | | 600/407 |
| 2015/0119708 A1 * | 4/2015 | Sachse | A61B 5/0071 |
| | | | 600/431 |
| 2016/0178680 A1 * | 6/2016 | Ntziachristos | A61B 5/0095 |
| | | | 73/643 |
| 2016/0206195 A1 * | 7/2016 | Huang | A61B 3/0025 |
| 2016/0220129 A1 * | 8/2016 | Ostroverkhov | A61B 5/0261 |
| 2016/0262674 A1 * | 9/2016 | Esenaliev | A61B 5/14552 |
| 2016/0317020 A1 * | 11/2016 | Liu | G01B 9/02076 |
| 2017/0100092 A1 * | 4/2017 | Kruse | A61B 8/0875 |
| 2017/0176393 A1 * | 6/2017 | O'Donnell | G01N 29/46 |
| 2017/0287175 A1 * | 10/2017 | Lin | G06T 11/008 |
| 2018/0172546 A1 * | 6/2018 | Calzavara | G01M 3/243 |
| 2019/0025258 A1 * | 1/2019 | Guibert | G01B 17/025 |

OTHER PUBLICATIONS http://download.ni.com/evaluation/pxi/Understanding%20FFTs%20and%20Windowing.pdf.*

Extended European Search Report, dated Feb. 3, 2017, regarding Application No. 16192876.7, 8 pages.

Bossi et al., "Ultrasound Inspection System for Inspecting a Test Object with Non-Planar Features," U.S. Appl. No. 13/526,853, filed Jun. 19, 2012, 62 pages.

Pelivanov et al., "A kHz rate pump-probe scanner for advanced evaluation of aircraft composites," International Symposium on Laser Ultrasonics and Advanced Sensing, paper No. 12, Jun. 2015, 3 pages.

Pelivanov et al., "A new fiber-optic non-contact compact laser-ultrasound scanner for fast non-destructive testing and evaluation of aircraft composites," Journal of Applied Physics, vol. 115, Mar. 2014, 12 pages.

Pelivanov et al., "NDT of fiber-reinforced composites with a new fiber-optic pump-probe laser-ultrasound system," Photoacoustics, vol. 2, Jan. 2014, 13 pages.

Extended European Search Report, dated May 31, 2017, regarding Application No. 16192876.7, 4 pages.

* cited by examiner

COMPOSITE INSPECTION

RELATED PROVISIONAL APPLICATION

This application claims the benefit of U.S. Provisional Patent Application Ser. No. 62/270,554, filed Dec. 21, 2015, and entitled "Composite Inspection."

BACKGROUND INFORMATION

1. Field

The present disclosure relates generally to non-destructive inspection and, in particular, to performing non-destructive inspection on a layered structure. Still more particularly, the present disclosure relates to a method and apparatus for detecting material changes in a composite structure.

2. Background

In manufacturing aircraft, vehicles, and other structures, inspection of parts used to form these structures is often performed to determine whether the parts will have desired parameters for a desired performance of the part. Additionally, the structures and parts are inspected as part of normal maintenance when the aircraft, vehicles, and other structures are in use.

Non-destructive testing is commonly performed on these parts. Non-destructive testing is used to evaluate the properties of a part without altering the ability to use the part in service.

Ultrasound testing is a type of non-destructive testing. Ultrasound testing is often used to perform inspections on aircraft parts that include, or are comprised of, composite materials. Ultrasound testing involves transmitting acoustic waves through a test object, such as an aircraft part or structure.

Ultrasound testing is commonly performed using a transducer. The transducer is configured to send acoustic waves into a test object and detect a response to the acoustic waves. The response to these acoustic waves is analyzed to determine whether inconsistencies are present in the test object.

Aircraft, cars, medical devices, and even clothing are being designed and manufactured with greater and greater percentages of composite materials. For example, composite materials are used in aircraft to decrease the weight of the aircraft. This decreased weight improves performance features such as payload capacity and fuel efficiency. Further, composite materials provide longer service life for various components in an aircraft. Composite materials may also decrease the weight of other items such as artificial limbs, bicycles, cars, body armor, or other desirable products.

Composite materials may be tough, light-weight materials created by combining two or more functional components. For example, a composite material may include reinforcing fibers bound in a polymer resin matrix. Resins used in composite materials may include thermoplastic or thermoset resins. The fibers may be unidirectional or may take the form of a woven cloth or fabric.

In manufacturing composite structures, layers of composite material are typically laid up on a tool. The layers may be comprised of fibers in sheets. These sheets may take the form of fabrics, tape, tows, or other suitable forms. In some cases, resin may be infused or preimpregnated into the sheets. These types of sheets are commonly referred to as prepreg. The different layers of prepreg may be laid up in different orientations, and different numbers of layers may be used depending on the performance requirements of the composite structure being manufactured.

Inconsistencies may be introduced to the composite structure during manufacturing or during use of the composite structure. Due to the regular spacing of the layers that make up the composite material, inspection of the composite material may be more difficult than desired for some locations or some types of inconsistencies.

Further, some inconsistencies may not be conventionally detectable using conventional non-destructive techniques. Therefore, it would be desirable to have a method and apparatus that take into account at least some of the issues discussed above, as well as other possible issues.

SUMMARY

In one illustrative embodiment, a method of detecting local material changes in a composite structure is presented. A pulsed laser beam is directed towards the composite structure comprised of a number of composite materials. Wide-band ultrasonic signals are formed in the composite structure when radiation of the pulsed laser beam is absorbed by the composite structure. The wide-band ultrasonic signals are detected to form data. The data is processed to identify a local frequency value for the composite structure. The local frequency value is used to determine if local material changes are present in the number of composite materials.

In another illustrative embodiment, a method is presented. A pulsed laser beam is directed towards a composite structure comprised of a plurality of layers. A number of wide-band ultrasonic signals are formed in the composite structure when radiation of the pulsed laser beam is absorbed by the composite structure. The wide-band ultrasonic signals are detected to form data. The data comprises a plurality of ultrasonic A-scans for at least a portion of the composite structure. A moving window in the time domain is applied to each of the plurality of ultrasonic A-scans to form windowed signals. A frequency measurement is determined within the windowed signals for each of the plurality of A-scans. The frequency measurement is averaged for all of the plurality of ultrasonic A-scans to form a frequency value for the composite structure. The frequency value is used to determine if the composite structure has a modified structural period.

In a further illustrative embodiment, a method is presented. A-scans for a composite structure are obtained using a laser ultrasound inspection system. A number of frequency measurements is determined for each of the A-scans. The number of frequency measurements for the each of the A-scans is averaged to form a frequency value for the composite structure. The frequency value is compared to a frequency value of a composite structure standard to determine if the composite structure has been exposed to an undesirable amount of stress.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The different illustrative embodiments recognize and take into account one or more different considerations. For example, the illustrative embodiments recognize and take into account that the performance of composite structures depend on both composition and fabrication quality. The illustrative embodiments further recognize and take into account that the structural properties of composite materials may be sensitive to irreversible chemical and mechanical degradation following stresses. The stresses may be thermal or mechanical. For example, thermal stresses may be placed on composite materials by lightning strikes, jet engine exhaust, fires, or other thermal incidences.

The illustrative embodiments recognize and take into account that thermal or mechanical stresses may cause material changes in the composite structure. These material changes may reduce the strength of the composite structure. The illustrative embodiments further recognize and take into account that composite materials may have reduced strength without any evident inconsistencies.

The illustrative embodiments recognize and take into account that conventional ultrasound and x-ray inspections may detect macroscopic flaws in composite materials. However, the illustrative embodiments also recognize and take into account that conventional ultrasound and x-ray inspections do not detect stress-induced material changes in a composite structure. The illustrative embodiments recognize and take into account that conventional inspection techniques that detect material changes may be limited to surface changes. Currently, no conventional inspection technique may evaluate the full composite material volume for stress-induced material changes.

Figure 1:
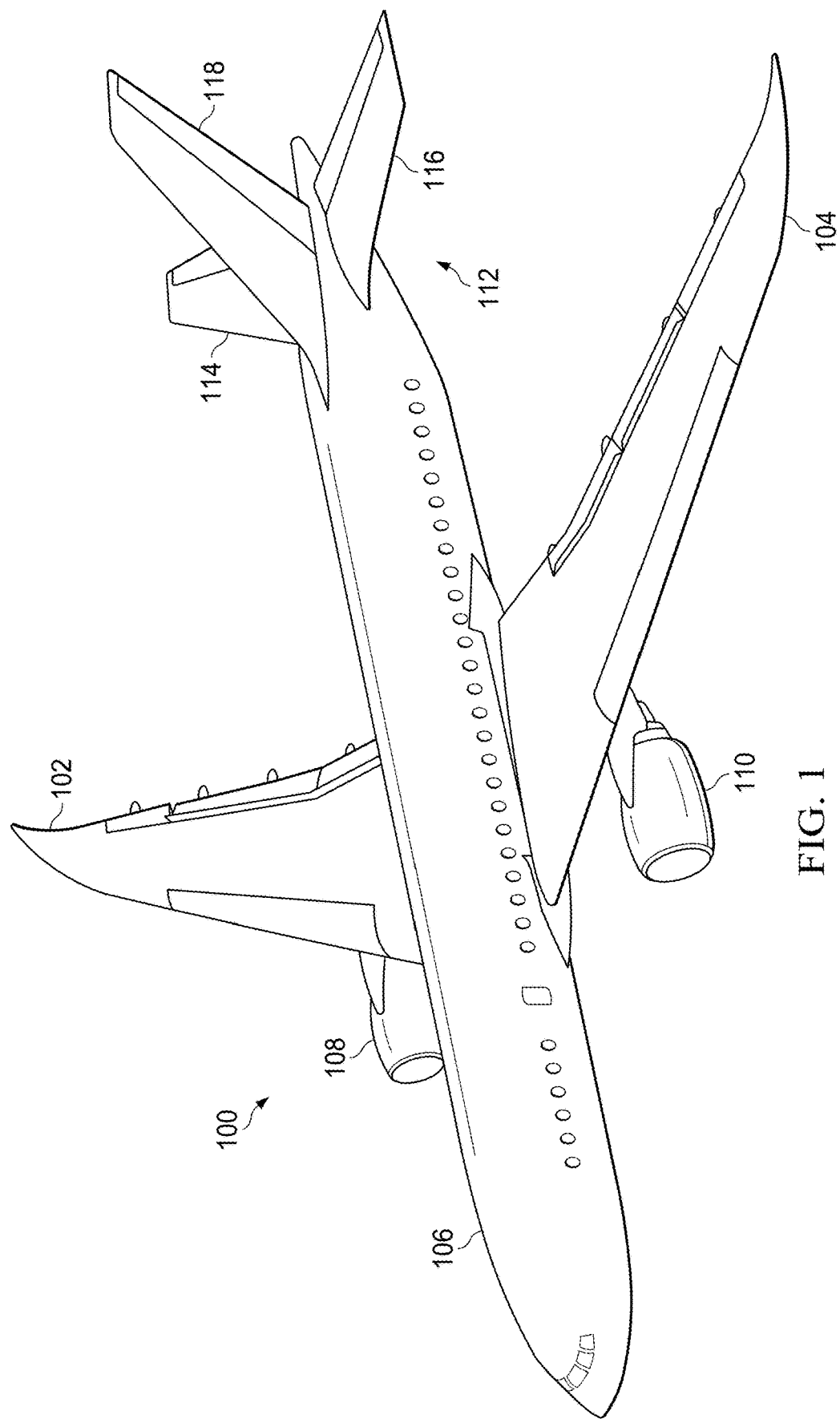
FIG. 1 is an illustration of an aircraft in which an illustrative embodiment may be implemented.

With reference now to the figures, and in particular, with reference to FIG. 1, an illustration of an aircraft is depicted in which an illustrative embodiment may be implemented. In this illustrative example, aircraft 100 has wing 102 and wing 104 attached to body 106. Aircraft 100 includes engine 108 attached to wing 102 and engine 110 attached to wing 104. Body 106 has tail section 112. Horizontal stabilizer 114, horizontal stabilizer 116, and vertical stabilizer 118 are attached to tail section 112 of body 106.

Aircraft 100 is an example of an aircraft having composite structures that may be inspected with a laser ultrasound inspection system in accordance with an illustrative embodiment. For example, composite skin in at least one of wing 102 or wing 104 may be inspected using a laser ultrasound inspection system.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, thing, or a category.

For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations.

This illustration of aircraft 100 is provided for purposes of illustrating one environment in which the different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, a rotorcraft, or other suitable types of aircraft.

Although the illustrative examples for an illustrative embodiment are described with respect to an aircraft, an illustrative embodiment may be applied to other types of platforms. The platform may be, for example, a mobile platform, a stationary platform, a land-based structure, an aquatic-based structure, or a space-based structure. More specifically, the platform may be a surface ship, a tank, a personnel carrier, a train, a spacecraft, a space station, a satellite, a submarine, an automobile, a manufacturing facility, a building, or other suitable platforms.

Further, an illustrative embodiment may be applied to other types of composite structures. For example, composite structures other than platforms may be inspected for material changes using a laser ultrasound inspection system. Composite structures other than platforms may include medical devices, prosthetic limbs, or any other desirable products for the screening, diagnosis, treatment, or prevention or any combination or sub-combination thereof of physical or mental health conditions in human beings or animals.

Figure 2:
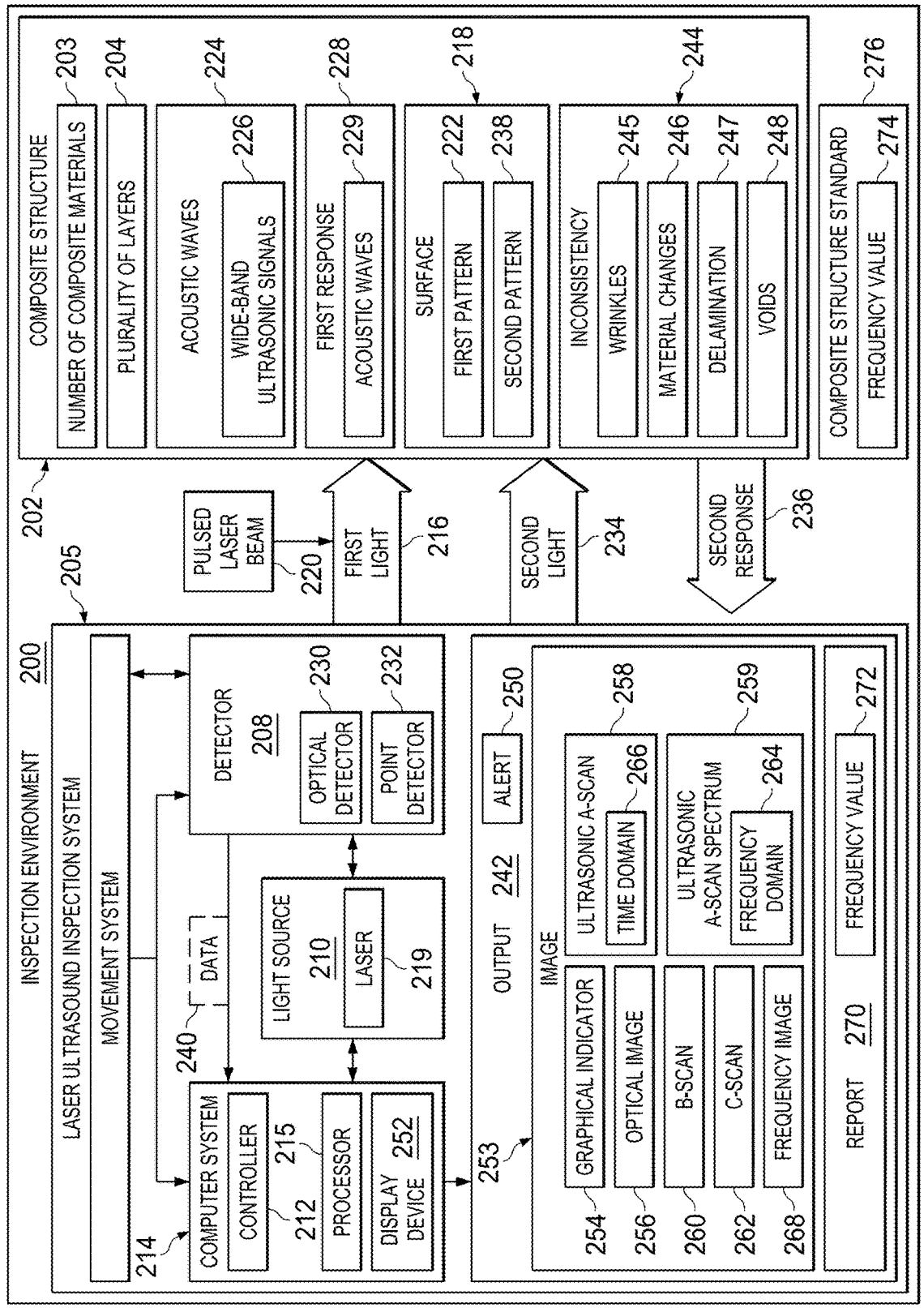
FIG. 2 is an illustration of a block diagram of an inspection environment in accordance with an illustrative embodiment.

With reference now to FIG. 2, an illustration of a block diagram of an inspection environment is depicted in accordance with an illustrative embodiment. As depicted, inspection environment 200 includes composite structure 202. Composite structure 202 may take any number of forms. For example, composite structure 202 may be a part for an aircraft. Composite structure 202 is comprised of number of composite materials 203. Further, composite structure 202 is formed of plurality of layers 204. In some illustrative examples, plurality of layers 204 has a substantially consistent thickness and spacing.

In these illustrative examples, composite structure 202 is a composite part for an aircraft selected from one of a panel, a fuselage barrel, a stringer, a spar, a rib, a wing box, a wing, a stabilizer, and other suitable types of parts. Composite structure 202 is inspected using laser ultrasound inspection system 205. As depicted, laser ultrasound inspection system 205 includes movement system 206, detector 208, light source 210, and controller 212.

In these illustrative examples, controller 212 controls the operation of laser ultrasound inspection system 205. Controller 212 may be implemented using hardware, software, firmware, or a combination thereof.

In these illustrative examples, controller 212 may be implemented within computer system 214. Computer system 214 may be one or more computers. When more than one computer is present in computer system 214, those computers may be in communication with each other through a communications medium such as a network.

When software is used, the operations performed by the controller may be implemented using, for example, without limitation, program code configured to run on a processor unit, such as processor 215. When firmware is used, the operations performed by the controller may be implemented using, for example, without limitation, program code and data and stored in persistent memory to run on a processor unit.

When hardware is employed, the hardware may include one or more circuits that operate to perform the operations performed by the controller. Depending on the implementation, the hardware may take the form of a circuit system, an integrated circuit, an application specific integrated circuit (ASIC), a programmable logic device, or some other suitable type of hardware device configured to perform any number of operations.

A programmable logic device may be configured to perform certain operations. The device may be permanently configured to perform these operations or may be reconfigurable. A programmable logic device may take the form of, for example, without limitation, a programmable logic array, a programmable array logic, a field programmable logic array, a field programmable gate array, or some other type of programmable hardware device.

In some illustrative examples, the operations and/or processes performed by the controller may be performed using organic components integrated with inorganic components. In some cases, the operations and/or processes may be performed by entirely organic components, excluding a human being. As one illustrative example, circuits in organic semiconductors may be used to perform these operations and/or processes.

Movement system 206 is configured to move light source 210 and detector 208 relative to composite structure 202. Movement system 206 may be implemented using a number of different types of systems. In one example, movement system 206 is a robot. The robot may be, for example, a robotic arm that may move detector 208 about a number of axes. Movement system 206 also may be, for example, without limitation, a gantry robot, a hand-operated scanning head, and other suitable types of movement systems.

Light source 210 is configured to transmit first light 216 onto surface 218 of composite structure 202. In some illustrative examples, light source 210 is laser 219. In one specific example, laser 219 is a diode-pumped nanosecond laser. When light source 210 takes the form of laser 219, first light 216 may be pulsed laser beam 220.

In this illustrative example, first light 216 is transmitted in a manner that forms first pattern 222 on surface 218 of composite structure 202. In these illustrative examples, first pattern 222 of first light 216 is a plurality of areas on which first light 216 illuminates on surface 218. These areas may be circular, oval, square, oblique, or have some other shape depending on the angle of projection onto the surface. In some illustrative examples, first pattern 222 takes the form of a line.

First light 216 is configured to form acoustic waves 224 within composite structure 202 when first light 216 encounters composite structure 202. Acoustic waves 224 occur when first light 216 is transmitted onto surface 218 of composite structure 202. For example, energy in first light 216 causes thermoelastic expansion in composite structure 202. The thermoelastic expansion results in acoustic waves 224 in composite structure 202.

In these illustrative examples, acoustic waves 224 are ultrasound sound waves. Thus, acoustic waves 224 are ultrasonic signals. More specifically, acoustic waves 224 take the form of wide-band ultrasonic signals 226. Acoustic waves 224 may have, for example, a frequency from about 20 kilohertz to about 100 megahertz depending on the particular implementation. The frequency for acoustic waves 224 depends on the material used to form composite structure 202, the pulse width of the laser excitation, and other suitable factors.

Additionally, detector 208 is configured to detect first response 228 to acoustic waves 224. First response 228 includes acoustic waves 229 that may occur as a result of scattering, reflection, modulation, and other changes to acoustic waves 224 traveling within composite structure 202. First response 228 is comprised of acoustic waves 229 that occur in response to acoustic waves 224. In this illustrative example, first response 228 is detected by detector 208.

In some illustrative examples, detector 208 takes the form of optical detector 230. In some illustrative examples, detector 208 is point detector 232. In one example, detector 208 may comprise any form of interferometer. For example, detector 208 includes a fiber-optic modified Sagnac interferometer for non-contact detection of backscattered ultrasound.

Detector 208 transmits second light 234 onto surface 218 of composite structure 202 and detects second response 236 to second light 234. In one illustrative example, second light 234 is transmitted in the form of second pattern 238 onto surface 218 of composite structure 202. In this illustrative example, second pattern 238 takes the form of a point.

Second response 236 is second light 234 that has been deflected by first response 228 in this illustrative example. First response 228, caused by acoustic waves 224 traveling within composite structure 202, reaches surface 218 and is detected. In some illustrative examples, the detection of first response 228 is detected using an interferometer that sends a reference light, such as second light 234 and detects the mechanical vibrations on surface 218 in second response 236. Detector 208 includes any desirable form of interferometer.

Detector 208 sends data 240 to controller 212 when second response 236 is detected. Data 240 is used by controller 212 to generate output 242. In some examples, data 240 includes a full-bandwidth signal for a location of composite structure 202 being inspected. When data 240 includes received signals for a plurality of locations of composite structure 202, data 240 includes a plurality of ultrasonic A-scans. As laser ultrasound inspection system 205 is scanned across composite structure 202, data 240 for a plurality of locations on composite structure 202 are collected.

As depicted, output 242 indicates whether inconsistency 244 is present in composite structure 202. Inconsistency 244 may be, for example, without limitation, wrinkles 245, material changes 246, delamination 247, voids 248, and other undesired features or properties in composite structure 202. In some illustrative examples, material changes 246 may be referred to as "local." Local material changes 246 refer to inconsistency 244 in an area of composite structure 202 that has been inspected using laser ultrasound inspection system 205. Material changes 246 result from at least one of thermal stresses or physical stresses on composite structure 202 prior to directing pulsed laser beam 220 towards the composite structure 202.

Output 242 may takes any desirable form. For example, output 242 may take the form of alert 250. Alert 250 indicates whether inconsistency 244 is present. Alert 250 may be displayed on display device 252 within computer system 214.

In another illustrative example, output 242 is image 253. Image 253 also may be displayed on display device 252. In one illustrative example, image 253 is an image of a portion or all of composite structure 202 with graphical indicator 254 when inconsistency 244 is present in composite structure 202. In one example, Graphical indicator 254 is displayed in a location in image 253 corresponding to a location in composite structure 202 where inconsistency 244 is detected. In other illustrative examples, if inconsistency 244 is absent, graphical indicator 254 may be displayed to indicate an absence of inconsistency 244.

In some illustrative examples, image 253 is optical image 256. Optical image 256 may be an image of surface 218 of composite structure 202.

In other illustrative examples, image 253 is a representation of a portion of composite structure 202. For example, image 253 is selected from ultrasonic A-scan 258, ultrasonic A-scan spectrum 259, B-scan 260, or C-scan 262. Ultrasonic A-scan 258 and ultrasonic A-scan spectrum 259 are each a graph. Ultrasonic A-scan spectrum 259 is displayed in frequency domain 264. Ultrasonic A-scan spectrum 259 is computed by Fourier transform of ultrasonic A-scan 258. Ultrasonic A-scan 258 is in time domain 266. Ultrasonic A-scan 258 in time domain 266 is obtained by performing an inverse Fourier transform on ultrasonic A-scan spectrum 259 in frequency domain 264. In one example, frequency domain 264 has an x-axis of frequency and a y-axis of amplitude. In one example, time domain 266 has an x-axis of time and a y-axis of amplitude.

In some illustrative examples, ultrasonic A-scan 258 may be a representation of data 240. As a result, data 240 may be said to include ultrasonic A-scan 258. In other illustrative examples, ultrasonic A-scan 258 may be a representation of a portion of data 240 after data 240 is processed.

Ultrasonic A-scan 258 is representative of a location of composite structure 202. Data from ultrasonic A-scan 258 is combined with data from a plurality of ultrasonic A-scans of different locations of composite structure 202 to form B-scan 260. B-scan 260 may be at least one of a color or a grayscale image. The value of each pixel in B-scan 260 is representative of an intensity of second response 236 of a corresponding location of composite structure 202.

In one example, B-scan 260 has an x-axis of scanning distance and a y-axis of time. B-scan 260 may be a representation of data 240 or a representation of data 240 after data 240 is processed.

C-scan 262 is representative of all or a portion of composite structure 202. In one example, C-scan 262 has the same two-dimensional shape as all or a portion of composite structure 202. In some illustrative examples, C-scan 262 is a grayscale image. In other illustrative examples, C-scan 262 is a color image. The value of each pixel in C-scan 262 is representative of any desirable information. In one example, the value of each pixel in C-scan 262 is representative of locations of inconsistency 244 in composite structure 202. More specifically, the value of each pixel in C-scan 262 may be representative of locations of material changes 246 in composite structure 202.

In another illustrative example, image 253 takes the form of frequency image 268. Frequency image 268 is similar to B-scan 260 in the x-axis and y-axis type. For example, frequency image 268 may have an x-axis of scanning distance and a y-axis of time. However, the intensity of each pixel in frequency image 268 is indicative of a frequency such as a mean frequency or a maximum frequency determined by processing data 240. Frequency image 268 indicates the presence of material changes 246 in a portion of composite structure 202 represented in frequency image 268.

In still another illustrative example, output 242 takes the form of report 270. Report 270 may identify any inconsistencies in composite structure 202. Report 270 also may include other information, such as locations of inconsistencies, types of inconsistencies, sizes of inconsistencies, and other suitable types of information.

In some illustrative examples, report 270 includes frequency value 272. Frequency value 272 is an average of mean frequencies or maximum frequencies for a portion of composite structure 202 or for all locations of composite structure 202 inspected using laser ultrasound inspection system 205. The sample volume of composite structure 202 to average for frequency value 272 is determined by at least one of the initial material properties, scale of inhomogeneities to detect, accuracy of measurements, or other characteristics. Frequency value 272 is representative of the presence or absence of material changes 246 in composite structure 202. Frequency value 272 may be referred to as "local." Local frequency value 272 is an average of local values of mean frequencies or maximum frequencies determined for a certain volume of material in which the local material changes 246 are to be determined.

In one example, frequency value 272 is compared to frequency value 274 of composite structure standard 276. Composite structure standard 276 has the same layup and materials as composite structure 202. Composite structure standard 276 is verified to have desirable structural properties. When frequency value 272 differs from frequency value 274 of composite structure standard 276, frequency value 272 may indicate material changes 246 in composite structure 202. Thus, output 242 may be at least one of alert 250, image 253, report 270, or other suitable types of output.

The illustration of manufacturing environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although inspection environment 200 includes composite structure 202, in some illustrative examples, inspection environment 200 may instead include a structure of any desirable material. For example, inspection environment 200 may include a structure made from any desirable material with a plurality of layers.

Figure 3:
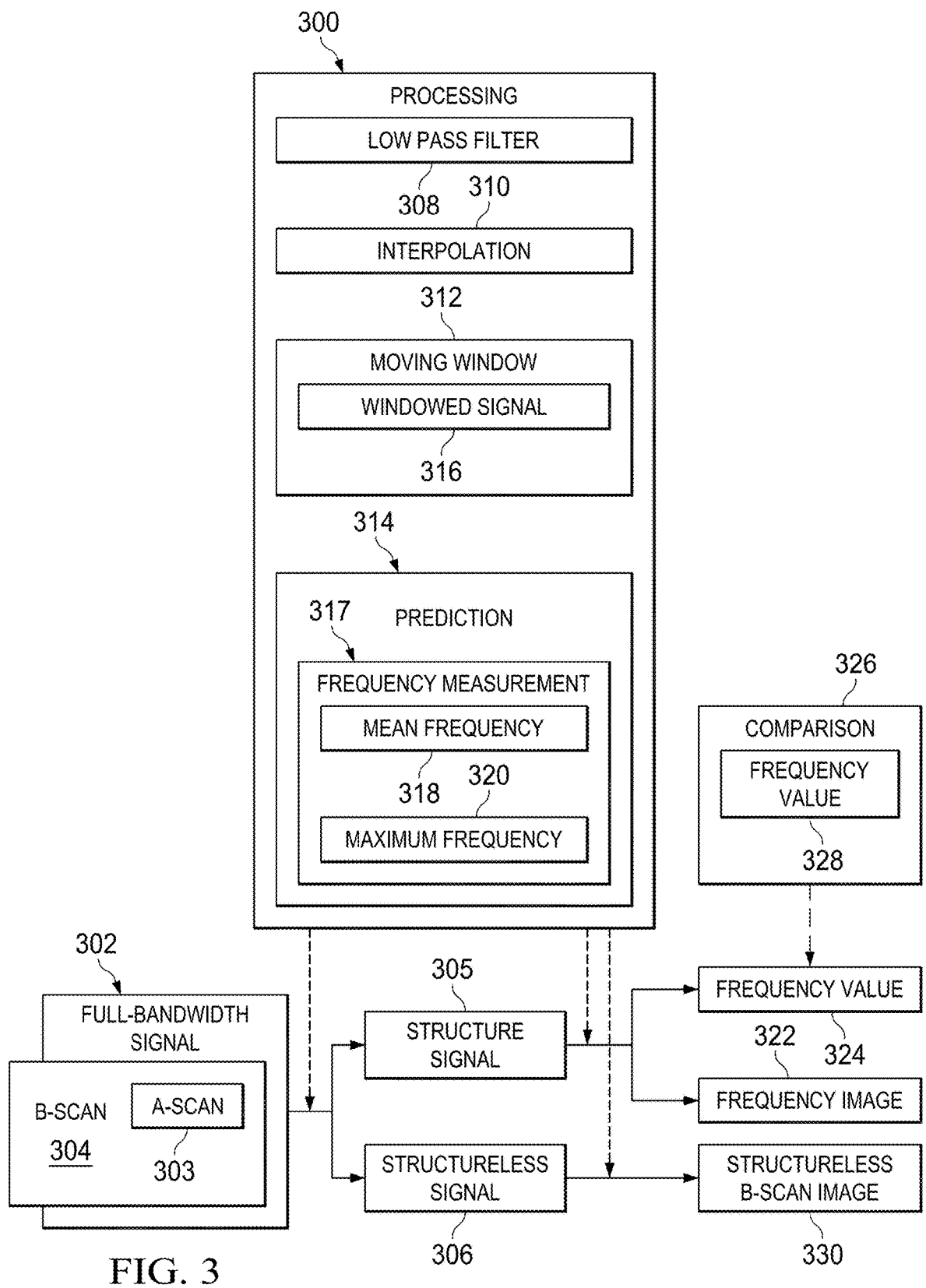
FIG. 3 is an illustration of a block diagram of processing of detector data in accordance with an illustrative embodiment.

Turning now to FIG. 3, an illustration of a block diagram of processing of detector data is depicted in accordance with an illustrative embodiment.

Processing 300 of full-bandwidth signal 302 may be performed in computer system 214 of FIG. 2. Full-band width signal 302 may be the data collected by detector 208. The detector used may limit the bandwidth in full-bandwidth signal 302. In one illustrative example, the detector bandwidth maximum may be 10 MHz. A detector may be selected such that an expected structure signal is positioned in full-bandwidth signal 302. For example, if an expected structure signal is approximately 7 MHz, the detection bandwidth should be higher than 7 MHz. Processing 300 of full-bandwidth signal 302 may be performed by processor 215 of FIG. 2.

Full-bandwidth signal 302 is all or part of data 240 of FIG. 2. In some illustrative examples, full-bandwidth signal 302 is referred to as A-scan 303. A-scan 303 is a portion of B-scan 304. B-scan 304 includes further A-scans other than A-scan 303. A-scan 303 is data for a first location on a composite structure. The further A-scans of B-scan 304 include other locations of the same composite structure.

Full-bandwidth signal 302 undergoes processing 300 to create one of structure signal 305 or structureless signal 306. Structure signal 305 is used to determine if material changes, such as material changes 246 of FIG. 2 are present in a structure with a plurality of regular layers. Structureless signal 306 increases detection of macroscopic inconsistencies in a structure with a plurality of layers. Structureless signal 306 depicts a clearer image of inconsistencies. In some illustrative examples, structureless signal 306 may be referred to as a structureless ultrasonic A-scan.

Processing 300 includes any desirable series of operations. For example, processing 300 includes at least one of low pass filter 308, interpolation 310, moving window 312, or prediction 314. The desirable series of operations of processing 300 are performed in any desirable order.

In one illustrative example, processing 300 on full-bandwidth signal 302 to form structure signal 305 includes moving window 312 and then prediction 314. In some illustrative examples, moving window 312 is a filter. In some illustrative examples, moving window 312 may be applied to A-scan 303 in the time domain.

Moving window 312 is applied to full-bandwidth signal 302 such that only a few signals of full-bandwidth signal 302 are contained within moving window 312 during a period of time. In some illustrative examples, moving window 312 is a Gaussian shape. The Gaussian shape provides an advantageous tradeoff between frequency resolution and time resolution. Frequency resolution provides for precise removal and interpolation in the frequency domain. Time resolution provides for spatial resolution in a frequency image.

Moving window 312 is described in terms of sampling size or time. A minimum window size for moving window 312 is the duration of the interrogating pulse. Moving window 312 is typically larger than this duration to get better spectral resolution in the frequency domain. Duration in time domain is inversely proportional to resolution in frequency domain. The choice of characteristics for moving window 312 is determined by a tradeoff between required resolution in the frequency domain and required resolution in the time domain. As discussed above, a Gaussian shape may optimize this tradeoff.

Moving window 312 is sized such that moving window 312 only contains a desired number of plies. In one example, moving window 312 contains any desirable number of plies from two to five plies. For example, moving window 312 contains three plies.

In one illustrative example, moving window 312 has a diameter of 35 sample points (1/e level, 5 ns per sample point), while time of flight within one ply of the composite structure is about 14 sample points. Thus, in this example, a windowed signal contains a few plies.

Each time moving window 312 is applied to full-bandwidth signal 302, windowed signal 316 is formed. For each windowed signal, prediction 314 may be performed. Prediction 314 determines frequency measurement 317. In one illustrative example, frequency measurement 317 is mean frequency 318. In another illustrative example, frequency measurement 317 is maximum frequency 320.

Mean frequency 318 may be determined using any desirable method. In one example, mean frequency 318 is determined using the autocorrelation function of the complex, analytic representation of windowed signal 316 of A-Scan 303, $\hat{R}(t)$, according to the following equation:

$$f_{mean} = \frac{1}{2\pi i} \frac{\dot{R}(0)}{R(0)} = \frac{1}{2\pi} \dot{\phi}(0) \tag{1}$$

R(0)—is the magnitude of the complex autocorrelation function, $\hat{R}(t)$, at time zero and $\emptyset(0)$ is the phase of the complex autocorrelation function at time zero. The dot above a function represents the time derivative of that function.

Mean frequency 318 is determined for each windowed signal 316 of full-bandwidth signal 302. Further, in some examples, mean frequency 318 is determined for other full-bandwidth signals other than full-bandwidth signal 302. For example, mean frequency 318 may be determined for each windowed signal 316 of each A-scan of B-scan 304.

In some illustrative examples, after determining mean frequency 318 of each windowed signal 316 of each A-scan of B-scan 304, the mean frequency 318 values are used to form frequency image 322. Frequency image 322 may be an implementation of frequency image 268 of FIG. 2. Frequency image 322 includes each mean frequency 318 of each windowed signal 316 of each A-scan of B-scan 304. Material changes may be evident in frequency image 322. For example, intensity of the pixels of frequency image 322 indicates material changes.

In some illustrative examples, after determining mean frequency 318 of each windowed signal 316 of each A-scan of B-scan 304, the mean frequency 318 values are used to determine frequency value 324. Frequency value 324 may be an average of all mean frequency 318 values for B-scan 304. Frequency value 324 may be indicative of material changes.

When frequency measurement 317 is maximum frequency 320, frequency value 324 may be an average of all maximum frequency 320 values for all or part of B-scan 304. Maximum frequency 320 may be predicted using any desirable method. In these illustrative examples, maximum frequency 320 is predicted using the following equation:

$$S_n = \Sigma_{k=1}^{p} a_k * S_{n-k} \qquad (2)$$

where p is a quantity of coefficients and $S_n$ is the A-scan signal at sample point n.

Frequency value 324 is used to determine whether material changes are present in an area of a composite structure represented by B-scan 304.
Determining if material changes are present includes comparison 326. Comparison 326 compares frequency value 324 to frequency value 328 of a composite structure standard, such as composite structure standard 276 of FIG. 2. Material changes are determined to be present if frequency value 324 differs from frequency value 328 of a composite structure standard.

For example, frequency value 324 changes with increased stress in the composite structure. As one example, frequency value 324 is lower for areas having a higher thermal stress. As another example, frequency value 324 changes for areas having a higher mechanical stress.

In another illustrative example, processing 300 on full-bandwidth signal 302 includes low pass filter 308 to create structureless signal 306. Low pass filter 308 is used to remove regular structure signals resulting in structureless signal 306. Structureless signal 306 is used to generate B-scan image 330. In this example, B-scan image 330 may be referred to as a low-pass filtered B-scan image. B-scan image 330 indicated macroscopic inconsistencies such as porosity, delamination, or other macroscopic inconsistencies.

In one illustrative example, low pass filter 308 is represented by:

$$\text{Filter}(f) = \left(1 - \exp\left(-\left(\frac{f}{f_0}\right)^2\right)\right) * \exp\left(-\left(\frac{f}{f_1}\right)^2 - \left(\frac{f}{f_2}\right)^4\right) \qquad (3)$$

In one illustrative example, the parameters may include: $f_0=100$ kHz, $f_1=11$ MHz, and $$\frac{f_2}{f_1} = 1.2$$

In some illustrative examples, instead of 11 MHz, $f_1=5$ MHz.

Figure 4:
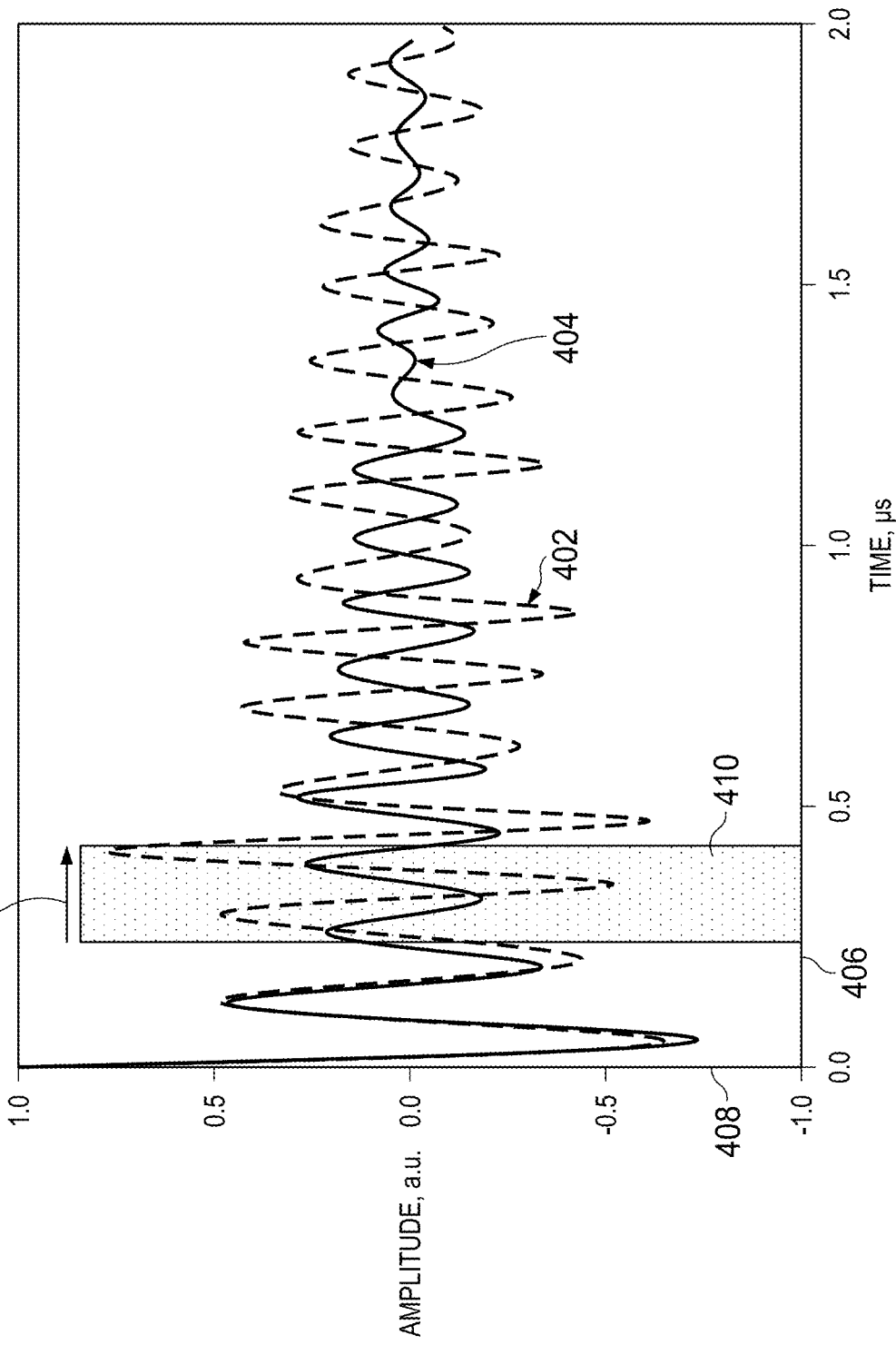
FIG. 4 is an illustration of an overlay of two ultrasonic A-scans in the time domain in accordance with an illustrative embodiment.

Turning now to FIG. 4, an illustration of an overlay of two ultrasonic A-scans in the time domain is depicted in accordance with an illustrative embodiment. Image 400 is a physical implementation of image 253 of FIG. 2. Image 400 includes A-scan 402 and A-scan 404. A-scan 402 and A-scan 404 are examples of ultrasonic A-scan 258 in time domain 266 of FIG. 2.

A-scan 402 comprises data for a first composite structure subjected to 600 degrees Fahrenheit. A-scan 404 comprises data for a second composite structure subjected to 200 degrees Fahrenheit. The first composite structure of A-scan 402 has the same layup as the second composite structure of A-scan 404. The first composite structure of A-scan 402 and the second composite structure of A-scan 404 have the same plies placed in the same order. As can be seen in image 400, A-scan 402 and A-scan 404 have different peak locations. Further, as can be seen in image 400, A-scan 402 and A-scan 404 have different peak values.

Image 400 has x-axis 406 and y-axis 408. In this example, A-scan 402 and A-scan 404 are in the time domain. Accordingly, x-axis 406 is time in microseconds and y-axis 408 is amplitude.

Moving window 410 is applied to each of A-scan 402 and A-scan 404 to determine frequency measurements. Frequency measurements are at least one of maximum frequencies or mean frequencies. Moving window 410 includes a number of plies of the composite structures. In this illustrative example, moving window 410 includes two plies for each of A-scan 402 and A-scan 404.

Moving window 410 is moved in direction 412 in image 400 to form a number of windowed signals.
Frequency measurements are determined for each windowed signal of both A-scan 402 and A-scan 404. The frequency measurements of A-scan 402 are used to determine a frequency value. The frequency value is used to determine whether material changes have occurred in the first composite structure of A-scan 402. Any material changes in the first composite structure (not depicted) of A-scan 402 may be due to thermal stresses. The frequency measurements of A-scan 404 are used to determine a frequency value. The frequency value is used to determine whether material changes have occurred in the second composite structure of A-scan 404. Any material changes in the second composite structure (not depicted) of A-scan 404 may be due to thermal stresses.

Figure 5:
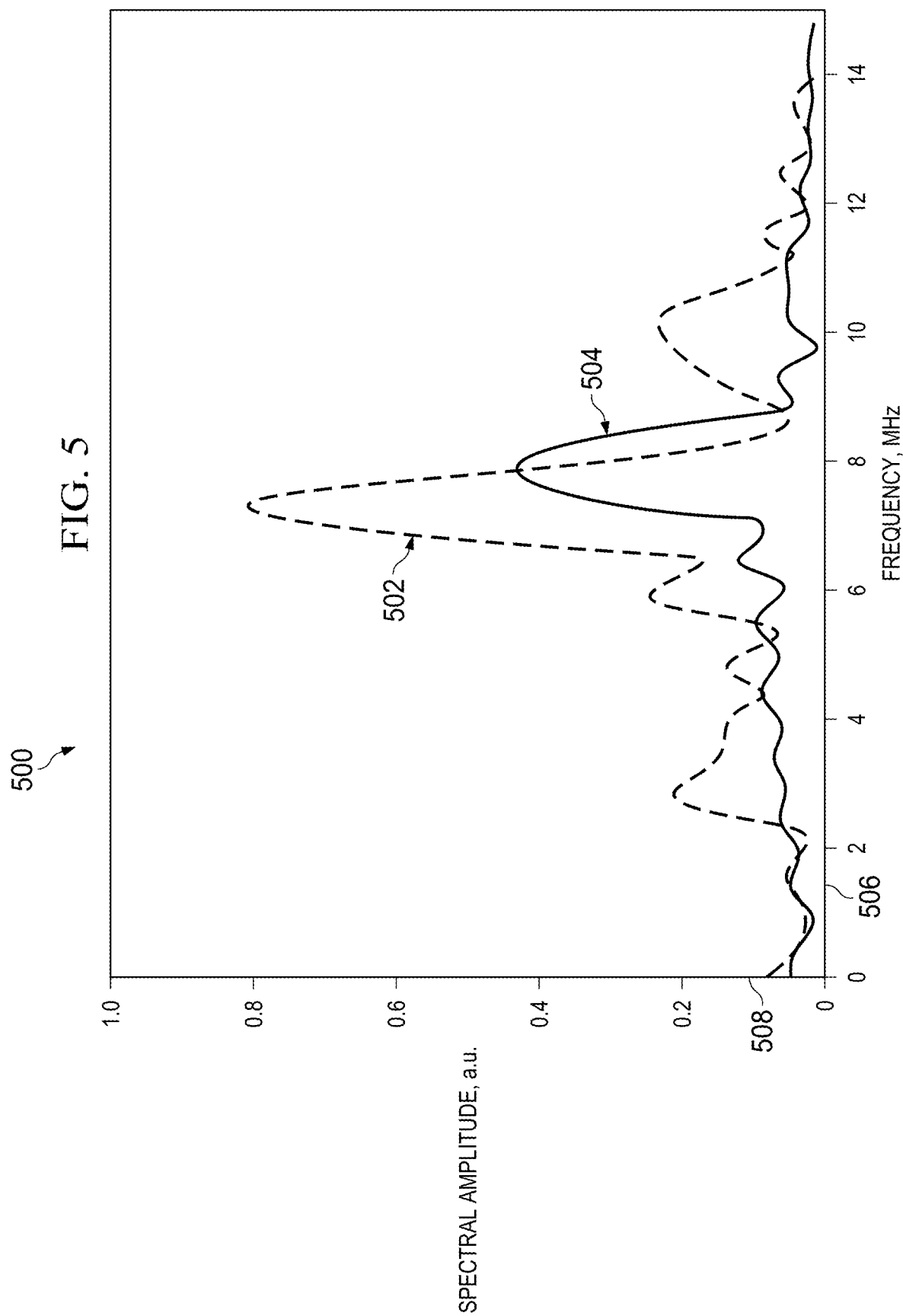
FIG. 5 is an illustration of an overlay of two ultrasonic A-scans in the frequency domain in accordance with an illustrative embodiment.

Turning now to FIG. 5, an illustration of an overlay of two ultrasonic A-scans in the frequency domain is depicted in accordance with an illustrative embodiment. Image 500 is a physical implementation of image 253 of FIG. 2. Image 500 includes A-scan 502 and A-scan 504. A-scan 502 and A-scan 504 are examples of ultrasonic A-scan 258 in frequency domain 264 of FIG. 2.

A-scan 502 is a view of A-scan 402 in the frequency domain. A-scan 504 is a view of A-scan 404 in the frequency domain. Image 500 has x-axis 506 and y-axis 508. X-axis 506 is frequency in MHz. Y-axis 508 is spectral amplitude.

As can be seen from image 500, A-scan 502 and A-scan 504 are significantly different. For example, A-scan 502 and A-scan 504 have different peak frequencies. Further, A-scan 502 and A-scan 504 have different secondary peaks.

Figure 6:
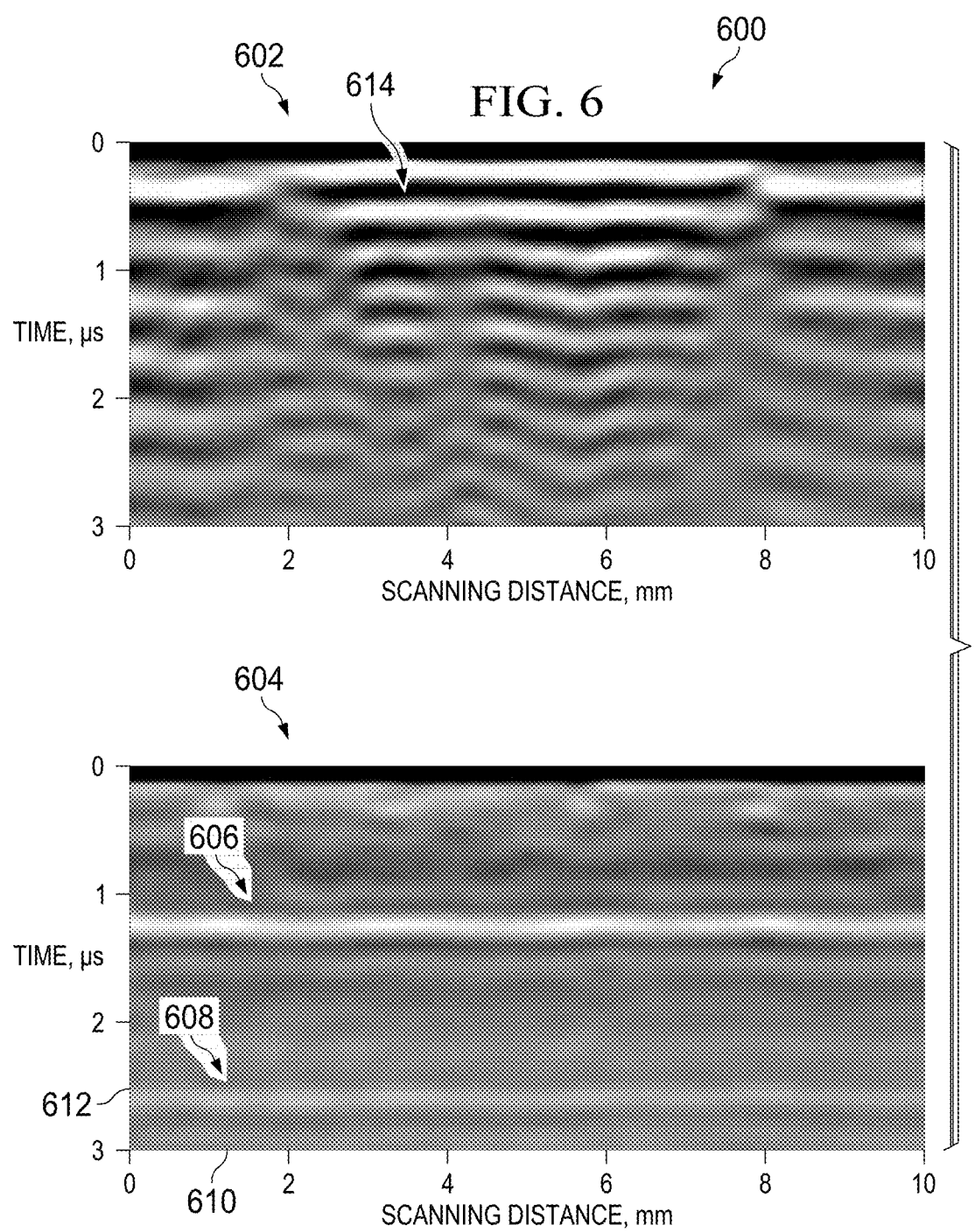
FIG. 6 is an illustration of two B-scans in accordance with an illustrative embodiment.

Turning now to FIG. 6, an illustration of two B-scans is depicted in accordance with an illustrative embodiment. More specifically, in FIG. 6, image 600 includes two low-pass filtered in the frequency range [0-5] MHz B-scans. Image 600 is a physical implementation of image 253 of FIG. 2. Image 600 includes B-scan 602 and B-scan 604. B-scan 602 and B-scan 604 are examples of B-scan 260 in FIG. 2.

B-scan 602 is a B-scan image of the first composite structure subjected to 600 degrees Fahrenheit. B-scan 604 is a B-scan image of the second composite structure subjected to 200 degrees Fahrenheit. B-scan 602 and B-scan 604 are low pass filtered B-scan images.

B-scan 604 does not have any visible inconsistencies. First back wall reflection 606 is visible in B-scan 604. Second back wall reflection 608 is also visible in B-scan 604. B-scan 604 has x-axis 610 and y-axis 612. X-axis 610 is scanning distance in millimeters. Y-axis 612 is time in microseconds.

B-scan 602 has visible inconsistencies. B-scan 602 includes full delamination 614. When a composite material has full delamination 614, the composite structure has undesirable performance. Full delamination 614 is not only visible in B-scan 602, but may also be visible to the naked eye when viewing the composite structure.

Although inconsistencies, such as full delamination 614, are usually visible in B-scan images, material changes without full delamination 614 may not be visible in B-scan images. For example, material changes may cause performance changes, but may not be visible in B-scan images. Material changes without full delamination 614 also are not visible to the naked eye.

In this illustrative example, the first composite structure in B-scan 602 was subjected to 600 degrees Fahrenheit and it resulted in full delamination 614. However, another composite structure may be subjected to a temperature less than 600 degrees Fahrenheit and have material changes without exhibiting full delamination. For example, a third composite structure subjected to 400 degrees Fahrenheit may not have delamination. However, the third composite structure may have material changes affecting the performance of the third composite structure. These material changes may not be visible in a B-scan. The illustrative embodiments recognize and take into account that it may be desirable to determine if material changes are present.

Figure 7:
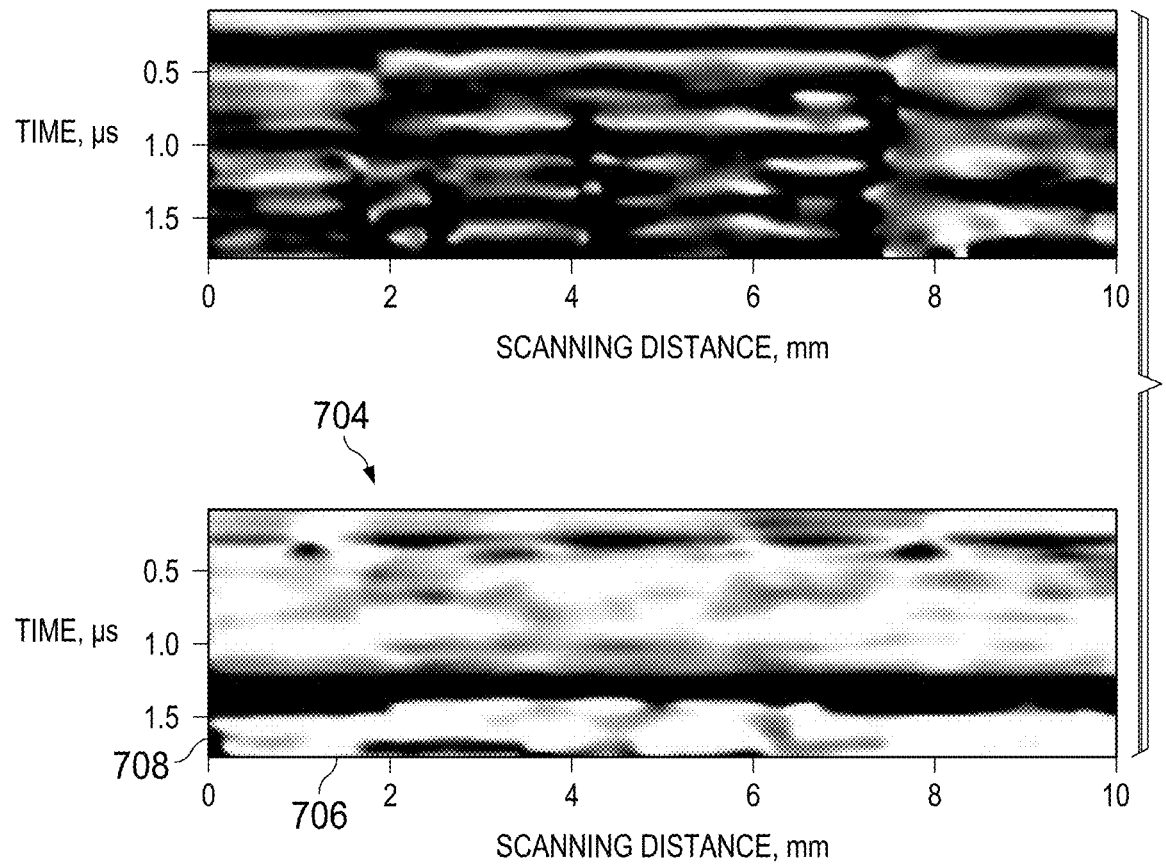
FIG. 7 is an illustration of two mean frequency images in accordance with an illustrative embodiment.

Turning now to FIG. 7, an illustration of two mean frequency images is depicted in accordance with an illustrative embodiment. Image 700 is a physical implementation of image 253 of FIG. 2. Image 700 includes frequency image 702 and frequency image 704. Frequency image 702 and frequency image 704 are examples of frequency image 268 in FIG. 2. Frequency image 702 and frequency image 704 have x-axis 706 and y-axis 708. As depicted, x-axis 706 is scanning distance in millimeters. Y-axis 708 is time in microseconds.

Frequency image 702 is an image of frequency measurements for the first composite structure subjected to 600 degrees Fahrenheit. In this illustrative example, the frequency measurements in frequency image 702 are maximum frequencies. Frequency image 704 is an image of frequency measurements for the first composite structure subjected to 200 degrees Fahrenheit. In this illustrative example, the frequency measurements in frequency image 704 are maximum frequencies. As can be seen in image 700, frequency image 702 and frequency image 704 are substantially different.

Figure 8:
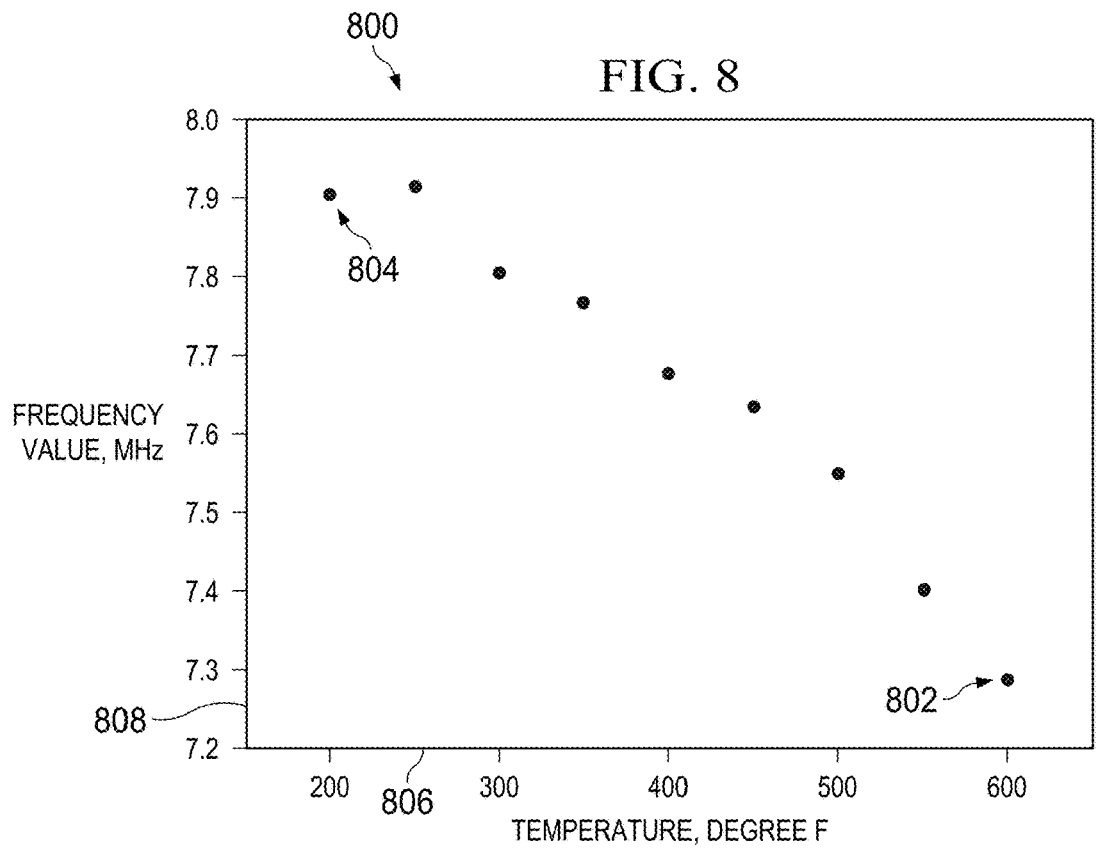
FIG. 8 is an illustration of a graph of frequency value versus temperature of a plurality of samples in accordance with an illustrative embodiment.

Turning now to FIG. 8, an illustration of a graph of frequency value versus temperature of a plurality of samples is depicted in accordance with an illustrative embodiment. Points 800 are implementations of frequency value 272 of FIG. 2 for a plurality of composite structures. Each of points 800 is a frequency value for a corresponding composite structure.

Point 802 is a data point for the first composite structure of FIGS. 4-7. Point 804 is a data point for the second composite structure of FIGS. 4-7. Points 800 are positioned on a graph with x-axis 806 and y-axis 808. X-axis 806 is temperature in degrees Fahrenheit. Y-axis 808 is frequency value.

As can be seen from points 800, increasing temperature to a composite structure affects the frequency value. As depicted, increasing the temperature to a composite structure causes the frequency value of a composite structure to decrease. Thus, the value of points 800 along y-axis 808 indicates whether material changes are present in a composite structure. As temperature of points 800 is associated with frequency value of points 800, material changes in a composite structure may be identified using a frequency value prior to full delamination occurring.

Quality testing may be performed on a variety of composite structures. By performing quality testing, frequency values are correlated to quality. Thus, in some illustrative examples, a subject composite structure is determined to have undesirable quality by comparing a frequency value of the subject composite structure to a frequency value limit. The frequency value limit may be a minimum frequency value for a desirable quality of a composite structure.

The different components shown in FIG. 1 and FIGS. 3-8 may be combined with components in FIG. 2, used with components in FIG. 2, or a combination of the two. Additionally, some of the components in FIG. 1 and FIGS. 3-8 may be illustrative examples of how components shown in block form in FIG. 2 may be implemented as physical structures.

Figure 9:
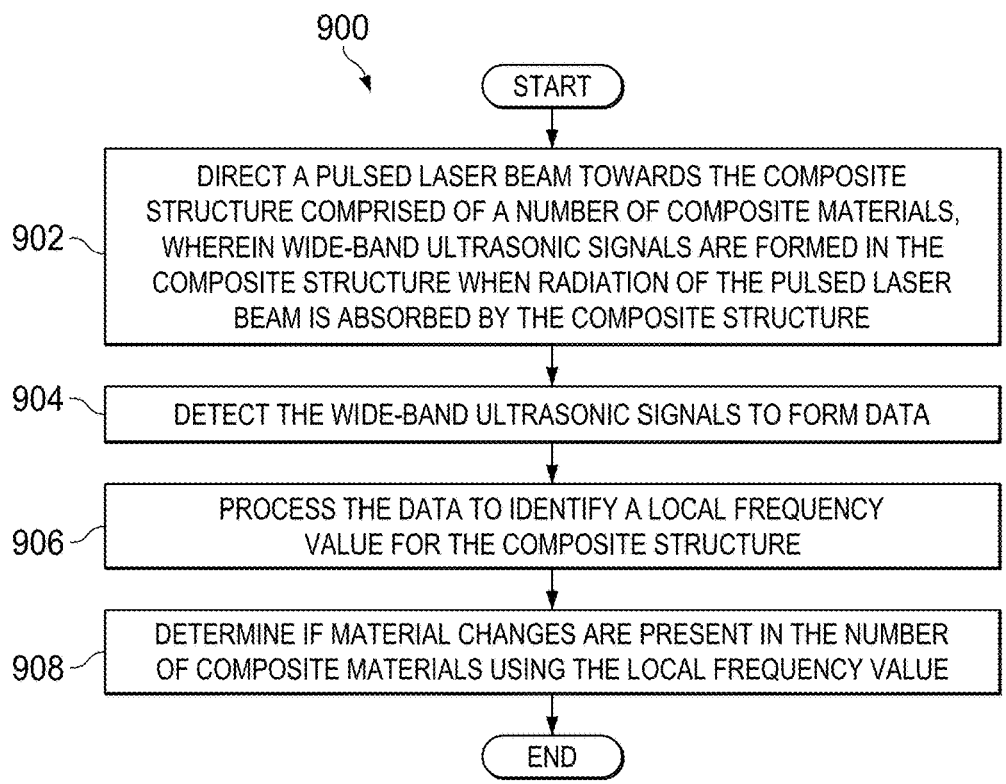
FIG. 9 is an illustration of a flowchart of a process for detecting material changes in a composite structure in accordance with an illustrative embodiment.

Turning now to FIG. 9, an illustration of a flowchart of a process for detecting material changes in a composite structure is depicted in accordance with an illustrative embodiment. The process illustrated in FIG. 9 may be implemented in an ultrasound inspection system such as laser ultrasound inspection system 205 in FIG. 2.

Process 900 begins by directing a pulsed laser beam towards the composite structure comprised of a number of composite materials, wherein wide-band ultrasonic signals are formed in the composite structure when radiation of the pulsed laser beam is absorbed by the composite structure (operation 902). In some examples, the material changes result from at least one of thermal stresses or physical stresses on the composite structure prior to directing the pulsed laser beam towards the composite structure.

Process 900 then detects the wide-band ultrasonic signals to form data (operation 904). In some illustrative examples, the wide-band ultrasonic signals are detected using a point-like optical detector of ultrasound. In some examples, the point-like optical detector of ultrasound is broadband.

Process 900 also processes the data to identify a local frequency value for the composite structure (operation 906). In some illustrative examples, the frequency value is an average of local values of mean frequencies or maximum frequencies determined for a certain volume of material in which material changes are to be determined. In some illustrative examples, identifying a local frequency value comprises determining a mean frequency of a windowed signal of an ultrasonic A-scan using the autocorrelation function of the complex, analytic representation of the windowed signal of the ultrasonic A-Scan, $\hat{R}(t)$, according to the following equation:

$$f_{mean} = \frac{1}{2\pi i} \frac{\dot{R}(0)}{R(0)} = \frac{1}{2\pi} \dot{\phi}(0) \quad (4)$$

where R(0) is the magnitude of the complex autocorrelation function, $\hat{R}(t)$, at time zero, and $\varnothing(0)$ is the phase of the complex autocorrelation function at time zero. The dot above a function represents the time derivative of that function.

Process 900 further determines if material changes are present in the number of composite materials using the local frequency value (operation 908). Afterwards, the process terminates. Determining if material changes are present in the number of composite materials may comprise comparing the frequency value to a frequency value of a composite structure standard. Material changes are determined to be present if the local frequency value differs from the frequency value of the composite structure standard. The frequency value of the composite structure standard may be representative of acceptable quality for the composite structure.

In some illustrative examples, if material changes are determined to be present, the material changes may be evaluated. For example, during an evaluation, the amount or extent of material changes may be determined. If the extent of material changes is acceptable, the composite structure may be monitored for any additional material changes in the future. If the extent of material changes is unacceptable, the composite structure may be reworked or replaced.

Figure 10:
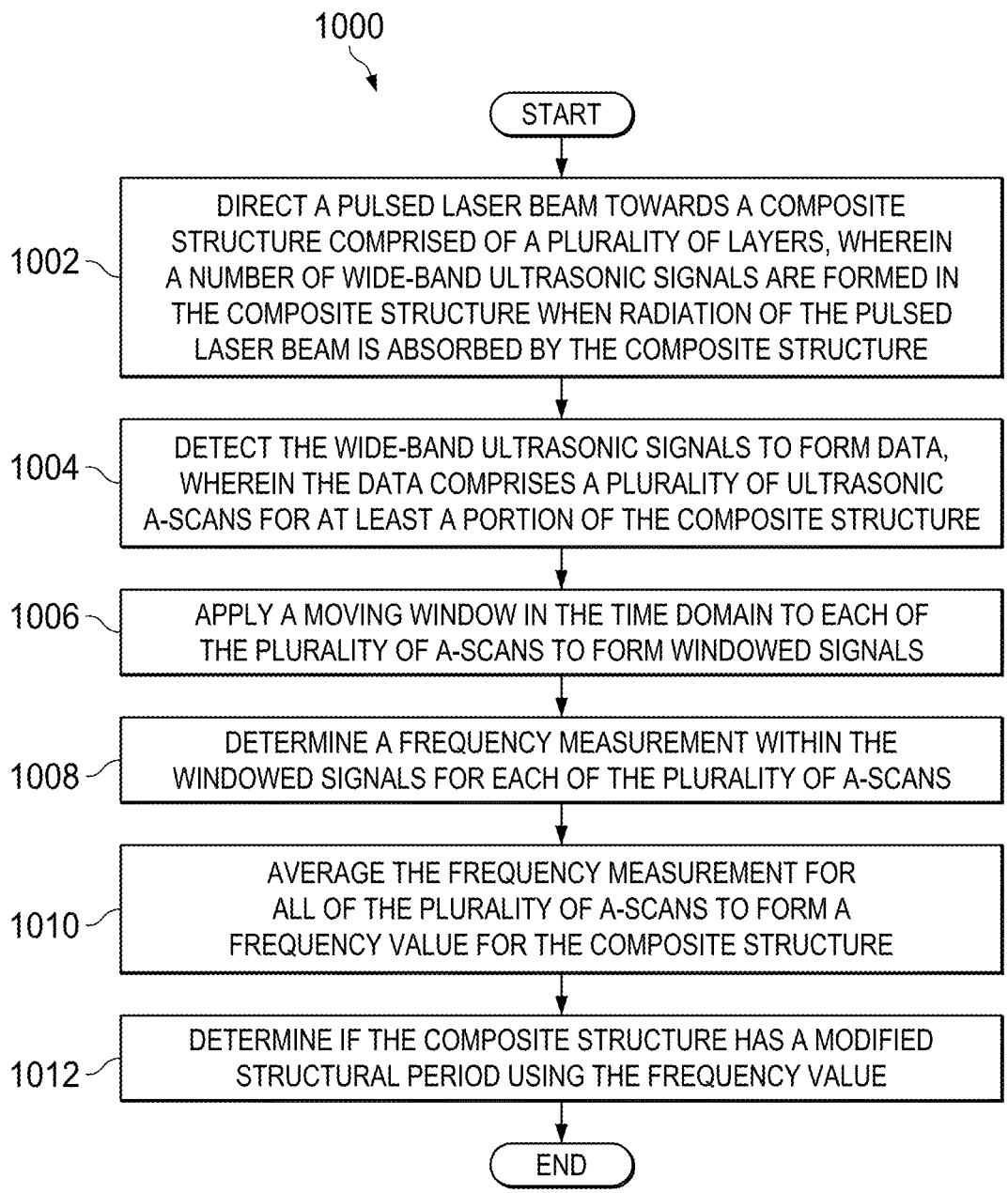
FIG. 10 is an illustration of a flowchart of a process for determining if a composite structure has a modified structural period in accordance with an illustrative embodiment.

Turning now to FIG. 10, an illustration of a flowchart of a process for determining if a composite structure has a modified structural period is depicted in accordance with an illustrative embodiment. The process illustrated in FIG. 10 may be implemented in an ultrasound inspection system such as laser ultrasound inspection system 205 in FIG. 2.

Process 1000 begins by directing a pulsed laser beam towards a composite structure comprised of a plurality of layers, wherein a number of wide-band ultrasonic signals are formed in the composite structure when radiation of the pulsed laser beam is absorbed by the composite structure (operation 1002). Process 1000 also detects the wide-band ultrasonic signals to form data, wherein the data comprises a plurality of ultrasonic A-scans for at least a portion of the composite structure (operation 1004).

Process 1000 applies a moving window in the time domain to each of the plurality of A-scans to form windowed signals (operation 1006). Process 1000 determines a frequency measurement within the windowed signals for each of the plurality of A-scans (operation 1008). In some illustrative examples, the frequency measurement is selected from a mean frequency or a maximum frequency. The mean frequency may be determined using the autocorrelation function of the complex, analytic representation of the windowed signal of the A-can, $\hat{R}(t)$, according to the equation:

$$f_{mean} = \frac{1}{2\pi i} \frac{\dot{R}(0)}{R(0)} = \frac{1}{2\pi} \dot{\phi}(0) \tag{5}$$

where R(0) is the magnitude of the complex autocorrelation function, $\hat{R}(t)$, at time zero and Ø(0) is the phase of the complex autocorrelation function at time zero, and the dot above a function represents the time derivative of that function.

Process 1000 also averages the frequency measurement for all of the plurality of A-scans to form a frequency value for the composite structure (operation 1010). Process 1000 determines if the composite structure has a modified structural period using the frequency value (operation 1012). Afterwards, the process terminates. In some illustrative examples, determining if the composite structure has a modified structural period using the frequency value comprises comparing the frequency value to a frequency value of a composite structure standard.

Figure 11:
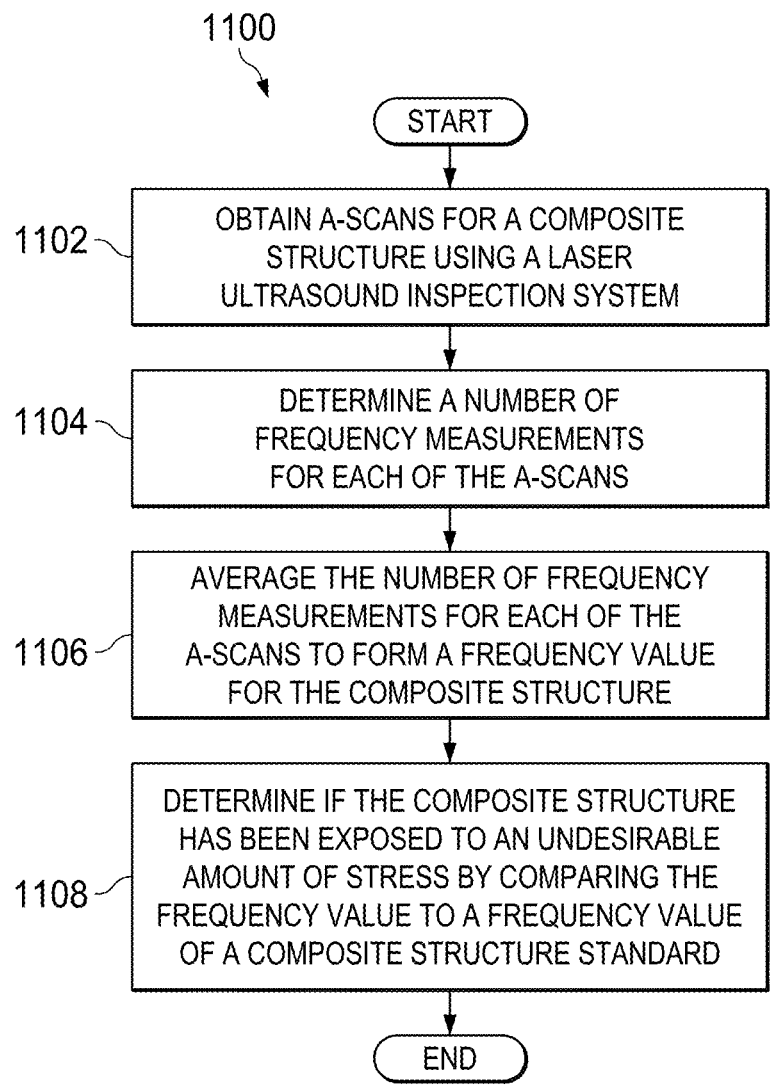
FIG. 11 is an illustration of a flowchart of a process for determining whether a composite structure has been exposed to an undesirable amount of stress in accordance with an illustrative embodiment.

Turning now to FIG. 11, an illustration of a flowchart of a process for determining whether a composite structure has been exposed to an undesirable amount of stress is depicted in accordance with an illustrative embodiment. The process illustrated in FIG. 11 may be implemented in an ultrasound inspection system such as laser ultrasound inspection system 205 in FIG. 2.

Process 1100 begins by obtaining A-scans for a composite structure using a laser ultrasound inspection system (operation 1102). In some examples, the composite structure has a plurality of layers having a structural period. In some illustrative examples, the structural period is altered with increased stress.

Process 1100 determines a number of frequency measurements for each of the A-scans (operation 1104). In some illustrative examples, the number of frequency measurements are a number of mean frequencies, and each mean frequency is determined using the autocorrelation function of the complex, analytic representation of the windowed A-Scan ($\hat{R}(t)$) according to the following equation:

$$f_{mean} = \frac{1}{2\pi i} \frac{\dot{R}(0)}{R(0)} = \frac{1}{2\pi} \dot{\phi}(0) \tag{6}$$

where R(0) is the magnitude of the complex autocorrelation function ($\hat{R}(t)$) at time zero and Ø(0) is the phase of the complex autocorrelation function at time zero, and the dot above a function represents the time derivative of that function.

Process 1100 averages the number of frequency measurements for the each of the A-scans to form a frequency value for the composite structure (operation 1106). Process 1100 then determines if the composite structure has been exposed to an undesirable amount of stress by comparing the frequency value to a frequency value of a composite structure standard (operation 1108). Afterwards the process terminates.

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

For example, the data in process 900 may comprise a number of ultrasonic A-scans of the composite structure. In this example, processing the data to identify the local frequency value may further comprise applying a moving window in a time domain to each of the number of ultrasonic A-scans to form windowed signals; determining at least one of a mean frequency or a maximum frequency of a Fourier spectrum taken for each of the windowed signals; and averaging at least one of the mean frequency or the maximum frequency from each of the windowed signals to form the frequency value. In another illustrative example, process 900 may further comprise displaying a B-scan, wherein the information displayed in the B-scan is the at least one of the mean frequency or the maximum frequency for each moving window. In one example, the moving window has a Gaussian shape.

Figure 12:
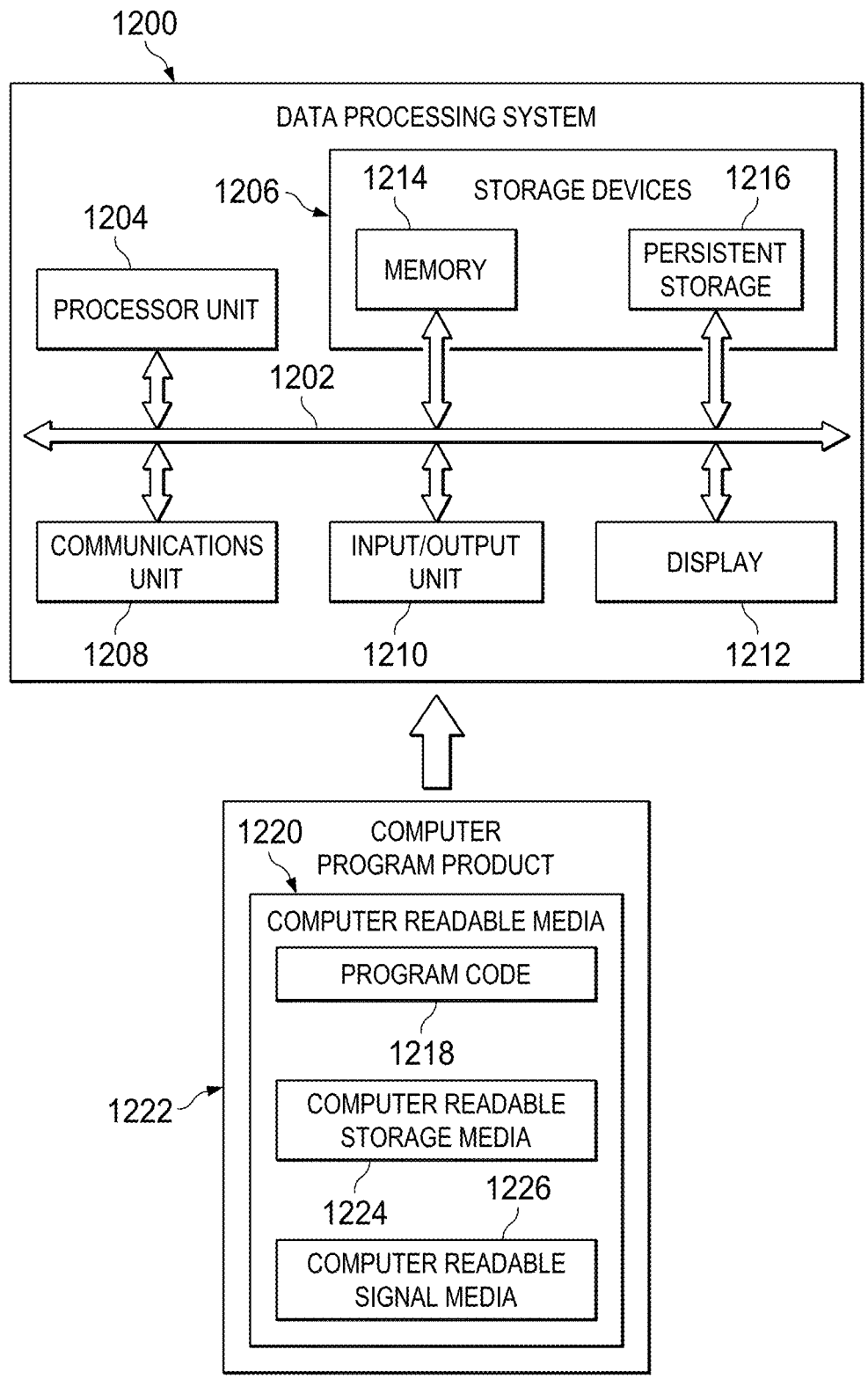
FIG. 12 is an illustration of a data processing system in the form of a block diagram in accordance with an illustrative embodiment.

Turning now to FIG. 12, an illustration of a data processing system in the form of a block diagram is depicted in accordance with an illustrative embodiment. Data processing system 1200 may be used to implement computer system 214 of FIG. 2. Data processing system 1200 may be used to process data as described in FIG. 3 and display output as depicted in FIGS. 4-8. As depicted, data processing system 1200 includes communications framework 1202, which provides communications between processor unit 1204, storage devices 1206, communications unit 1208, input/output unit 1210, and display 1212. In some cases, communications framework 1202 may be implemented as a bus system.

Processor unit 1204 is configured to execute instructions for software to perform a number of operations. Processor unit 1204 may comprise a number of processors, a multiprocessor core, and/or some other type of processor, depending on the implementation. In some cases, processor unit 1204 may take the form of a hardware unit, such as a circuit system, an application specific integrated circuit (ASIC), a programmable logic device, or some other suitable type of hardware unit.

Instructions for the operating system, applications, and/or programs run by processor unit 1204 may be located in storage devices 1206. Storage devices 1206 may be in communication with processor unit 1204 through communications framework 1202. As used herein, a storage device, also referred to as a computer readable storage device, is any piece of hardware capable of storing information on a temporary and/or permanent basis. This information may include, but is not limited to, data, program code, and/or other information.

Memory 1214 and persistent storage 1216 are examples of storage devices 1206. Memory 1214 may take the form of, for example, a random access memory or some type of volatile or non-volatile storage device. Persistent storage 1216 may comprise any number of components or devices. For example, persistent storage 1216 may comprise a hard drive, a flash memory, a rewritable optical disk, a rewritable magnetic tape, or some combination of the above. The media used by persistent storage 1216 may or may not be removable.

Communications unit 1208 allows data processing system 1200 to communicate with other data processing systems and/or devices. Communications unit 1208 may provide communications using physical and/or wireless communications links.

Input/output unit 1210 allows input to be received from and output to be sent to other devices connected to data processing system 1200. For example, input/output unit 1210 may allow user input to be received through a keyboard, a mouse, and/or some other type of input device. As another example, input/output unit 1210 may allow output to be sent to a printer connected to data processing system 1200.

Display 1212 is configured to display information to a user. Display 1212 may comprise, for example, without limitation, a monitor, a touch screen, a laser display, a holographic display, a virtual display device, and/or some other type of display device.

In this illustrative example, the processes of the different illustrative embodiments may be performed by processor unit 1204 using computer-implemented instructions. These instructions may be referred to as program code, computer usable program code, or computer readable program code, and may be read and executed by one or more processors in processor unit 1204.

In these examples, program code 1218 is located in a functional form on computer readable media 1220, which is selectively removable, and may be loaded onto or transferred to data processing system 1200 for execution by processor unit 1204. Program code 1218 and computer readable media 1220 together form computer program product 1222. In this illustrative example, computer readable media 1220 may be computer readable storage media 1224 or computer readable signal media 1226.

Computer readable storage media 1224 is a physical or tangible storage device used to store program code 1218 rather than a medium that propagates or transmits program code 1218. Computer readable storage media 1224 may be, for example, without limitation, an optical or magnetic disk or a persistent storage device that is connected to data processing system 1200.

Alternatively, program code 1218 may be transferred to data processing system 1200 using computer readable signal media 1226. Computer readable signal media 1226 may be, for example, a propagated data signal containing program code 1218. This data signal may be an electromagnetic signal, an optical signal, and/or some other type of signal that can be transmitted over physical and/or wireless communications links.

The illustration of data processing system 1200 in FIG. 12 is not meant to provide architectural limitations to the manner in which the illustrative embodiments may be implemented. The different illustrative embodiments may be implemented in a data processing system that includes components in addition to or in place of those illustrated for data processing system 1200. Further, components shown in FIG. 12 may be varied from the illustrative examples shown.

Figure 13:
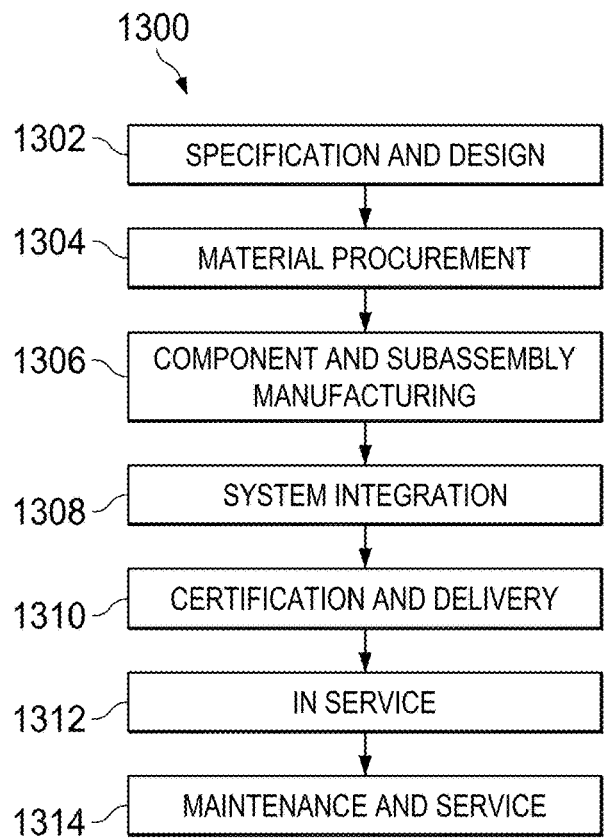
FIG. 13 is an illustration of an aircraft manufacturing and service method in the form of a block diagram in accordance with an illustrative embodiment.
Figure 14:
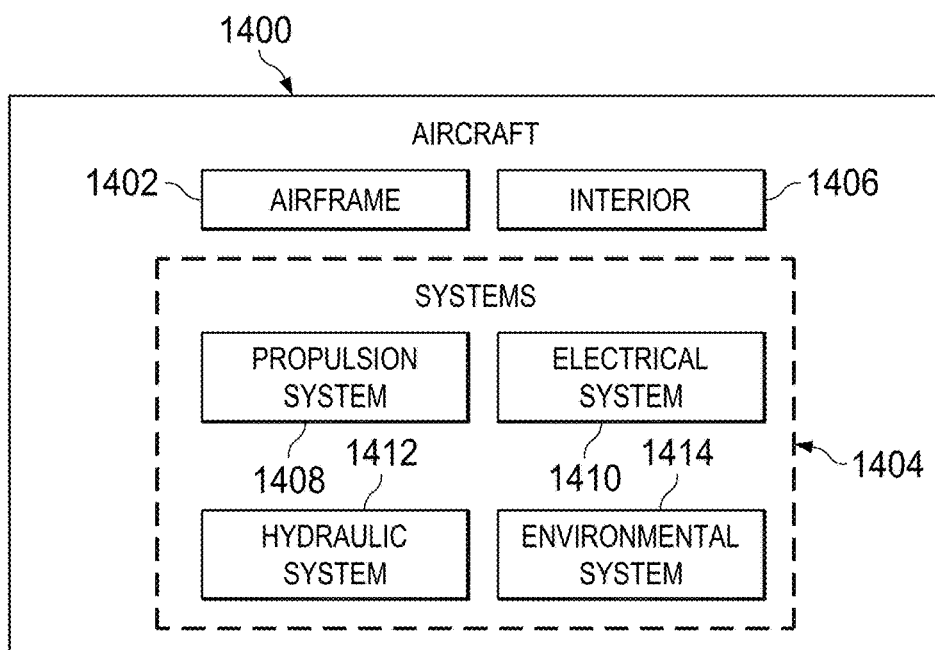
FIG. 14 is an illustration of an aircraft in the form of a block diagram in which an illustrative embodiment may be implemented.

Illustrative embodiments of the disclosure may be described in the context of aircraft manufacturing and service method 1300, as shown in FIG. 13, and aircraft 1400, as shown in FIG. 14. Turning first to FIG. 13, an illustration of an aircraft manufacturing and service method is depicted in accordance with an illustrative embodiment. During preproduction, aircraft manufacturing and service method 1300 may include specification and design 1302 of aircraft 1400 and material procurement 1304.

During production, component and subassembly manufacturing 1306 and system integration 1308 of aircraft 1400 takes place. Thereafter, aircraft 1400 may go through certification and delivery 1310 in order to be placed in service 1312. While in service 1312 by a customer, aircraft 1400 is scheduled for routine maintenance and service 1314, which may include modification, reconfiguration, refurbishment, and other maintenance or service.

Each of the processes of aircraft manufacturing and service method 1300 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 14, an illustration of an aircraft is depicted in which an illustrative embodiment may be implemented. In this example, aircraft 1400 is produced by aircraft manufacturing and service method 1300 in FIG. 13, and may include airframe 1402 with plurality of systems 1404 and interior 1406. Examples of plurality of systems 1404 include one or more of propulsion system 1408, electrical system 1410, hydraulic system 1412, and environmental system 1414. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1300 in FIG. 13. One or more illustrative embodiments may be used during component and subassembly manufacturing 1306 in FIG. 13. For example, laser ultrasound inspection system 205 in FIG. 2 may be used to inspect composite structures during component and subassembly manufacturing 1306. Further, laser ultrasound inspection system 205 in FIG. 2 may be used to inspect an assembly during maintenance and service 1314 in FIG. 13. For example, composite structures of aircraft 1400 may be inspected during scheduled maintenance for aircraft 1400 using laser ultrasound inspection system 205.

Thus, one or more illustrative embodiments provide a method and apparatus for determining if material changes are present in a composite structure. Material changes occur in a composite structure as a result of mechanical or thermal stresses. Material changes may not be observable using conventional ultrasound techniques. However, material changes influence material strength and other material properties. As a result, material changes due to thermal stresses may undesirably impact a composite structure.

The one or more illustrative embodiments provide a method for determining a frequency value. The frequency value is used to determine if material changes are present in a composite structure. The frequency value is compared to a frequency value of a composite structure standard to determine if material changes are present. If a frequency value of the composite structure differs from the frequency value of the composite structure standard, then material changes are determined to be present in the composite structure.

The frequency value is an average of frequency measurements for a portion of the composite structure inspected using the laser ultrasound inspection system. The frequency measurements are at least one of maximum frequencies or mean frequencies.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method of detecting non-evident inconsistencies that reduce a strength of a composite structure, the method comprising:
   directing a pulsed laser beam towards the composite structure comprised of a number of composite materials and thereby forming wide-band ultrasonic signals in the composite structure when radiation of the pulsed laser beam is absorbed by the composite structure;
   detecting, using a detector configured to receive a response to a deflection from the wide-band ultrasonic signals of a light generated by the detector, the deflection forming a number of ultrasonic A-scans of the composite structure;
   processing the ultrasonic A-scans and identifying a local frequency value for the composite structure, via:
      sizing a diameter of a moving window sufficient to comprise a number of sample points and applying the moving window in a time domain to each of the number of ultrasonic A-scans to produce a windowed A-scan signal sized to contain between two and five plies of the number of composite materials;
      determining at least one of a mean frequency or a maximum frequency of a Fourier spectrum taken for each of the windowed A-scan signals; and
   averaging at least one of: the mean frequency, or the maximum frequency, from each of the windowed A-scan signals and forming the local frequency value indicating a structural period of the composite structure; and
   determining if local material changes prior to a delamination of the composite structure, are present in the number of composite materials, via using the local frequency value and a frequency value of a composite structure standard.

2. The method of claim 1, further comprising comparing the local frequency value to the frequency value of the composite structure standard.

3. The method of claim 2, wherein the local material changes are determined to be present if the local frequency value differs from the frequency value of the composite structure standard.

4. The method of claim 3, wherein the local frequency value and the frequency value of the composite structure standard are within a range from 7-8 Mhz.

5. The method of claim 2, wherein the frequency value of the composite structure standard is representative of acceptable quality for the composite structure.

6. The method of claim 1 further comprising:
   displaying a B-scan, wherein information displayed in the B-scan is the at least one of the mean frequency or the maximum frequency for each moving window.

7. The method of claim 1, wherein identifying the local frequency value comprises:
   determining a mean frequency of the windowed A-scan signal using a complex autocorrelation function of a complex, analytic representation of the windowed signal of the ultrasonic A-Scan, $\hat{R}(t)$, according to an equation, $$f_{mean} = \frac{1}{2\pi i} \frac{\dot{\hat{R}}(0)}{\hat{R}(0)} = \frac{1}{2\pi} \dot{\phi}(0),$$

where $\hat{R}(0)$ is a magnitude of the complex autocorrelation function, $\hat{R}(t)$, at time zero, $\emptyset(0)$ is a phase of the complex autocorrelation function at time zero, and a dot above a function represents a time derivative of that function.

8. The method of claim 1, wherein the local frequency value is an average of local values of mean frequencies or maximum frequencies determined for a certain volume of material in which the local material changes are to be determined.

9. The method of claim 1, wherein the local material changes result from at least one of thermal stresses or physical stresses on the composite structure prior to directing the pulsed laser beam towards the composite structure.

10. The method of claim 1, wherein the wide-band ultrasonic signals are detected using a point-like optical detector of ultrasound.

11. The method of claim 10, wherein the point-like optical detector of ultrasound is broadband.

12. The method of claim 1, further comprising a duration of each pulse of the pulsed laser beam being equal to or less than 140 nano-seconds.

13. A method comprising:
directing a pulsed laser beam towards a composite structure comprised of a plurality of layers and thereby forming a number of wide-band ultrasonic signals in the composite structure when radiation of the pulsed laser beam is absorbed by the composite structure;
detecting the number of wide-band ultrasonic signals to form data, wherein the data comprises a plurality of ultrasonic A-scans for at least a portion of the composite structure;
sizing a diameter of a moving window sufficient to comprise a number of sample points to and applying the moving window in a time domain to each of the plurality of ultrasonic A-scans to produce a windowed A-scan signal sized to contain between two and five plies of the plurality of layers;
determining at least one of a mean frequency or a maximum frequency within the windowed A-scan signal for each of the plurality of ultrasonic A-scans;
averaging at least one of the mean frequency or the maximum frequency for all of the plurality of ultrasonic A-scans to form a frequency value that indicates a structural period for the composite structure; and
determining, using a local frequency value, if local material changes, relative to a standard structural period, to the structural period that reveal non-evident inconsistencies reducing a strength of the composite structure, prior to a delamination, are present in the portion of the composite structure.

14. The method of claim 13, further comprising comparing the local frequency value to the frequency value of the composite structure standard.

15. The method of claim 14, wherein the local frequency value and the frequency value of the composite structure standard are within a range from 7-8 Mhz.

16. The method of claim 13, wherein the mean frequency is determined using a complex autocorrelation function of a complex, analytic representation of the windowed signal of an A-Scan, $\hat{R}(t)$, according to an equation, $$f_{mean} = \frac{1}{2\pi i} \frac{\dot{R}(0)}{R(0)} = \frac{1}{2\pi} \dot{\phi}(0),$$

where R(0) is a magnitude of the complex autocorrelation function, $\hat{R}(t)$, at time zero, $\emptyset(0)$ is a phase of the complex autocorrelation function at time zero, and a dot above a function represents a time derivative of that function.

17. A method of inspecting a composite laminate, the method comprising:
obtaining, using a laser ultrasound inspection system, a plurality of ultrasonic A-scans for a composite structure, via:
directing a pulsed laser beam, from a laser, towards the composite structure comprising a plurality of layers absorbing a radiation from the pulsed laser beam and thereby generating a number of wide-band ultrasonic signals in the composite structure causing thermoelastic expansion within the composite structure; and
detecting, using a detector configured for noncontact detection of backscattered ultrasound, the number of wide-band ultrasonic signals; and forming the plurality of ultrasonic A-scans for at least a portion of the composite structure;
sizing a diameter of a moving window sufficient to comprise a number of sample points to and applying the moving window in a time domain to each of the plurality of ultrasonic A-scans to form a windowed A-scan signal sized to contain between two and five plies of a number of composite materials in the composite structure;
determining at least one of a mean frequency or a maximum frequency within time-windowed A-scan signals for each of the plurality of ultrasonic A-scans;
averaging at least one of the mean frequency or the maximum frequency for each of the plurality of ultrasonic A-scans to form a frequency value that indicates a structural period for the composite structure; and
determining if the composite structure has been exposed to an undesirable amount of stress via identifying local material changes, relative to a standard structural period, in and reducing a strength of the composite structure.

18. The method of claim 17, further comprising the composite structure comprising a plurality of layers comprising a structural period.

19. The method of claim 18, wherein the structural period is altered with increased stress.

20. The method of claim 17, wherein each mean frequency is determined using a complex autocorrelation function of a complex, analytic representation of a windowed A-Scan, ($\hat{R}(t)$), according to an equation, $$f_{mean} = \frac{1}{2\pi i} \frac{\dot{R}(0)}{R(0)} = \frac{1}{2\pi} \dot{\phi}(0),$$

where R(0) is a magnitude of the complex autocorrelation function, ($\hat{R}(t)$), at time zero, $\emptyset(0)$ is a phase of the complex autocorrelation function at time zero, and a dot above a function represents a time derivative of that function.

21. The method of claim 17, wherein the frequency value that indicates the structural period for the composite structure lies within a 7-8 MHz range.

* * * * *